United States Patent
Awasthi et al.

(10) Patent No.: US 12,012,238 B2
(45) Date of Patent: Jun. 18, 2024

(54) PACKAGING SOLUTIONS

(71) Applicant: Bausch + Lomb Ireland Limited, Dublin (IE)

(72) Inventors: Alok K. Awasthi, Pittsford, NY (US); Jade J. Russell, Perry, NY (US); Mark R. Mis, Rush, NY (US)

(73) Assignee: BAUSCH + LOMB IRELAND LIMITED (IE)

( * ) Notice: Subject to any disclaimer, the term of this patent is extended or adjusted under 35 U.S.C. 154(b) by 233 days.

(21) Appl. No.: 17/714,393

(22) Filed: Apr. 6, 2022

(65) Prior Publication Data

US 2022/0411115 A1 Dec. 29, 2022

Related U.S. Application Data

(60) Provisional application No. 63/193,325, filed on May 26, 2021.

(51) Int. Cl.
*B65B 25/00* (2006.01)
*A45C 11/00* (2006.01)
*B65B 55/04* (2006.01)
*B65D 85/00* (2006.01)

(52) U.S. Cl.
CPC .......... *B65B 25/008* (2013.01); *A45C 11/005* (2013.01); *B65B 55/04* (2013.01); *B65D 85/54* (2013.01); *B65D 2585/545* (2013.01)

(58) Field of Classification Search
CPC ....... B65B 25/008; B65B 55/04; B65D 85/54; B65D 2585/545; A45C 11/005
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 4,113,224 A | 9/1978 | Clark et al. |
| 4,136,250 A | 1/1979 | Mueller et al. |
| 4,153,641 A | 5/1979 | Deichert et al. |
| 4,197,266 A | 4/1980 | Clark et al. |
| 4,555,732 A | 11/1985 | Tuhro |
| 4,740,533 A | 4/1988 | Su et al. |
| 4,910,277 A | 3/1990 | Bambury et al. |
| 4,954,587 A | 9/1990 | Mueller |
| 5,010,141 A | 4/1991 | Mueller |
| 5,034,461 A | 7/1991 | Lai et al. |
| 5,070,215 A | 12/1991 | Bambury et al. |
| 5,079,319 A | 1/1992 | Mueller |
| 5,260,000 A | 11/1993 | Nandu et al. |
| 5,271,876 A | 12/1993 | Ibar |
| 5,310,779 A | 5/1994 | Lai |
| 5,321,108 A | 6/1994 | Kunzler et al. |
| 5,358,995 A | 10/1994 | Lai et al. |
| 5,387,662 A | 2/1995 | Kunzler et al. |
| 5,449,729 A | 9/1995 | Lai |
| 5,512,205 A | 4/1996 | Lai |
| 5,610,252 A | 3/1997 | Bambury et al. |
| 5,616,757 A | 4/1997 | Bambury et al. |
| 5,708,094 A | 1/1998 | Lai et al. |
| 5,710,302 A | 1/1998 | Kunzler et al. |
| 5,714,557 A | 2/1998 | Kunzler et al. |
| 5,908,906 A | 6/1999 | Kunzler et al. |
| 6,517,933 B1 | 2/2003 | Soane et al. |
| 7,674,782 B2 | 3/2010 | Suda et al. |
| 9,309,357 B2 | 4/2016 | Awasthi et al. |
| 2003/0044468 A1 | 3/2003 | Cellesi et al. |
| 2006/0106104 A1* | 5/2006 | Vehige ..................... A61K 9/08 514/738 |
| 2007/0149428 A1* | 6/2007 | Ammon, Jr. ............ A61L 12/06 510/112 |
| 2008/0307751 A1* | 12/2008 | Newman ............... C11D 3/0078 53/425 |
| 2017/0173012 A1 | 6/2017 | Bilstein et al. |
| 2018/0147283 A1* | 5/2018 | Claret ................... A61K 31/385 |
| 2019/0099441 A1* | 4/2019 | Mahler .................. A61K 45/06 |
| 2019/0328698 A1 | 10/2019 | Gallois-Bernos et al. |
| 2020/0000954 A1* | 1/2020 | Awasthi ............... A45C 11/005 |
| 2020/0339710 A1* | 10/2020 | Awasthi ............... A61K 31/728 |
| 2021/0087384 A1 | 3/2021 | DiBella, Jr. et al. |

FOREIGN PATENT DOCUMENTS

| | | |
|---|---|---|
| CN | 111518627 A | 8/2020 |
| CN | 111991415 A | 11/2020 |
| EP | 3412276 | 12/2018 |

(Continued)

OTHER PUBLICATIONS

Sigma-Aldrich.com "Product information Ectoine", URL: https://www.sigmaaldrich.com/deepweb/assets/sigmaaldrich/product/documents/301/819/e2271pis.pdf, Jan. 16, 2014.

Lai, Yu-Chin, "The Role of Bulky Polysiloxanylalkyl Methacryates in Polyurethane-Polysiloxane Hydrogels," Journal of Applied Polymer Science, 1996, pp. 1193-1199, vol. 60.

Priyesh Jain et al., "Poly(ectoine) Hydrogels Resist Nonspecific Protein Adsorption" Langmuir, 2017, 33, pp. 11264-11269.

Bloomage BioTech Brochure, www.bloomagebioactive.com, Jan. 2021, 2 pages.

Marc Benjamin Hahn et al., "Combined influence of ectoine and salt: spectroscopic and numerical evidence for compensating effects on aqueous solutions", Phys. Chem. Chem. Phys., 2016, 18, pp. 28398-28402.

(Continued)

*Primary Examiner* — Andrew M Tecco
*Assistant Examiner* — Nicholas E Igbokwe
(74) *Attorney, Agent, or Firm* — Michael E. Carmen; John E. Thomas

(57) ABSTRACT

A packaging system for the storage of an ophthalmic device is disclosed. The packaging system includes a sealed container containing one or more unused ophthalmic devices immersed in an aqueous packaging solution that includes ectoine or an ophthalmologically acceptable ectoine derivative. The aqueous packaging solution has an osmolality of at least about 150 mOsm/kg, a pH of about 6 to about 9 and is sterilized.

22 Claims, No Drawings

(56) References Cited

FOREIGN PATENT DOCUMENTS

| WO | 9631792 A1 | 10/1996 |
|---|---|---|
| WO | 20150162552 A1 | 10/2015 |
| WO | 2019006398 A2 | 1/2019 |

OTHER PUBLICATIONS

Ruediger Graf et al., "The multifunctional role of ectoine as a natural cell protectant", Clinics in Dermatology (2008) 26, 326-333.
Mridula Dwivedi et al., "Biophysical investigations of the structure and function of the tear fluid lipid layer and the effect of ectoine. Part A: Naturalmeibomian lipid films", Biochimica et Biophysica Acta 1838 (2014) 2708-2715.
A. K. Awasthi et al., "Ethylenically unsaturated polycarbosiloxanes for novel silicone hydrogels: synthesis, endgroup analysis, contact lens formulations, and structure-property correlations", Polym. Adv. Technol. 2013, 24 557-567.
Park et al., "Facile Syntheses of L-α-Glycerophosphorylcholine", Bull. Korean Chem. Soc. 2010, vol. 31, No. pp. 9 2689-2691.
Jan Lindberg, et al., Efficient Synthesis of Phospholipids from Glycidyl Phosphates, J. Org. Chemistry, 2002, 67, pp. 194-199.
Qinghai Zhang et al., "Microscale NMR Screening of New Detergents for Membrane Protein Structural Biology", Journal of the American Chemical Society, 2008, 130(23), pp. 7357-7363.
B. Xu, "Bloomecto™ Ectoine and Ocular Applications," Bloomage Biotechnology Corporation Limited, www.bloomagebioactive.com, Dec. 2020, 42 pages.

\* cited by examiner

PACKAGING SOLUTIONS

PRIORITY CLAIM

The present application claims priority to U.S. Provisional Patent Application Ser. No. 63/193,325, entitled "Packaging Solutions," filed May 26, 2021, the content of which is incorporated by reference herein in its entirety.

BACKGROUND

Blister-packs and glass vials are typically used to individually package each soft contact lens for sale to a customer. Saline or deionized water is commonly used to store the lens in the blister-packs. Because lens material may tend to stick to itself and to the lens package, packaging solutions for blister-packs have sometimes been formulated with various components to reduce or eliminate lens folding and sticking.

SUMMARY

In accordance with an illustrative embodiment, a packaging system for the storage of an ophthalmic device comprises a sealed container containing one or more unused ophthalmic devices immersed in an aqueous packaging solution comprising ectoine or an ophthalmologically acceptable ectoine derivative; wherein the aqueous packaging solution has an osmolality of at least about 150 mOsm/kg, a pH of about 6 to about 9 and is sterilized.

In accordance with another illustrative embodiment, a packaging system for storage of an ophthalmic device comprises a sealed container containing one or more unused ophthalmic devices immersed in an aqueous packaging solution comprising ectoine or an ophthalmologically acceptable ectoine derivative and one or more of a glycosaminoglycan and a modified glycosaminoglycan; wherein the aqueous packaging solution has an osmolality of at least about 150 mOsm/kg, a pH of about 6 to about 9 and is sterilized.

In accordance with yet another illustrative embodiment, a method of preparing a packaging system comprising a storable, sterile ophthalmic device comprises:
(a) providing an ophthalmic device;
(b) immersing the ophthalmic device in an aqueous packaging solution comprising ectoine or an ophthalmologically acceptable ectoine derivative; wherein the aqueous packaging solution has an osmolality of at least about 150 mOsm/kg and a pH in the range of about 6 to about 9;
(c) packaging the aqueous packaging solution and the ophthalmic device in a manner preventing contamination of the ophthalmic device by microorganisms; and
(d) sterilizing the packaged solution and ophthalmic device.

In accordance with still yet another illustrative embodiment, a method of preparing a packaging system comprising a storable, sterile ophthalmic device comprises:
(a) providing an ophthalmic device;
(b) immersing the ophthalmic device in an aqueous packaging solution comprising ectoine or an ophthalmologically acceptable ectoine derivative and one or more of a glycosaminoglycan and a modified glycosaminoglycan; wherein the aqueous packaging solution has an osmolality of at least about 150 mOsm/kg and a pH in the range of about 6 to about 9;
(c) packaging the aqueous packaging solution and the ophthalmic device in a manner preventing contamination of the ophthalmic device by microorganisms; and
(d) sterilizing the packaged solution and ophthalmic device.

DETAILED DESCRIPTION

The illustrative embodiments described herein are directed to packaging systems for the storage of ophthalmic devices intended for direct contact with body tissue or body fluid, e.g., direct contact in the eye. It is highly desirable that an ophthalmic device such as a contact lens be as comfortable as possible for wearers. Manufacturers of contact lenses are continually working to improve the comfort of the lenses. Nevertheless, many people who wear contact lenses still experience dryness or eye irritation throughout the day and particularly towards the end of the day. An insufficiently wetted lens at any point in time will cause significant discomfort to the lens wearer. Although wetting drops can be used as needed to alleviate such discomfort, it would certainly be desirable if such discomfort did not arise in the first place.

Accordingly, these problems are overcome by the illustrative embodiments disclosed herein which provide an improved packaging system for ophthalmic devices such as a contact lens such that the lens would be more lubricious and comfortable to wear in actual use thereby allowing for extended wear of the lens without irritation or other adverse effects to the cornea. Thus, in non-limiting illustrative embodiments, an aqueous packaging solution for use in a packaging system for ophthalmic devices as disclosed herein containing at least ectoine or an ophthalmologically acceptable ectoine derivative is believed to provide improved lubricity and/or wettability of an ophthalmic device. The ophthalmic device will therefore be more comfortable to wear in actual use and allow for extended wear of the lens without adverse effects to the cornea. Hydrophilic and/or lubricious surfaces of the ophthalmic devices herein such as contact lenses substantially prevent or limit the adsorption of tear lipids and proteins on, and their eventual absorption into, the lenses, thus preserving the clarity of the contact lenses. This, in turn, preserves their performance quality thereby providing a higher level of comfort to the wearer.

As used herein, the term "ophthalmic device" refers to devices that reside in or on the eye. These lenses can provide optical correction, wound care, drug delivery, diagnostic functionality or cosmetic enhancement or effect or a combination of these properties. Representative examples of such devices include, but are not limited to, soft contact lenses, e.g., a soft, hydrogel lens; soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking. Any material known to produce an ophthalmic device including a contact lens can be used herein.

The ophthalmic devices for use in the packaging systems disclosed herein can be any material known in the art capable of forming an ophthalmic device as described above. In an embodiment, an ophthalmic device includes devices which are formed from material not hydrophilic per se. Such devices are formed from materials known in the art and include, by way of example, polysiloxanes, perfluoropolyethers, fluorinated poly(meth)acrylates or equivalent fluorinated polymers derived, e.g., from other polymerizable carboxylic acids, polyalkyl(meth)acrylates or equivalent alkylester polymers derived from other polymerizable carboxylic acids, or fluorinated polyolefins, such as fluorinated ethylene propylene polymers, or tetrafluoroethylene, preferably in combination with a dioxol, e.g., perfluoro-2,2-dimethyl-1,3-dioxol. Representative examples of suitable bulk materials include, but are not limited to, lotrafilcon A, neofocon, pasifocon, telefocon, silafocon, fluorsilfocon, paflufocon, silafocon, elastofilcon, fluorofocon or Teflon® AF materials, such as Teflon® AF 1600 or Teflon® AF 2400 which are copolymers of about 63 to about 73 mol % of perfluoro-2,2-dimethyl-1,3-dioxol and about 37 to about 27 mol % of tetrafluoroethylene, or of about 80 to about 90 mol % of perfluoro-2,2-dimethyl-1,3-dioxol and about 20 to about 10 mol % of tetrafluoroethylene.

In another embodiment, an ophthalmic device includes a device which is formed from material hydrophilic per se, since reactive groups, e.g., carboxy, carbamoyl, sulfate, sulfonate, phosphate, amine, ammonium or hydroxy groups, are inherently present in the material and therefore also at the surface of an ophthalmic device manufactured therefrom. Such devices are formed from materials known in the art and include, by way of example, polyhydroxyethyl acrylate, polyhydroxyethyl methacrylate (HEMA), polyvinyl pyrrolidone (PVP), polyacrylic acid, polymethacrylic acid, polyacrylamide, polydimethylacrylamide (DMA), polyvinyl alcohol and the like and copolymers thereof, e.g., from two or more monomers selected from hydroxyethyl acrylate, hydroxyethyl methacrylate, N-vinyl pyrrolidone, acrylic acid, methacrylic acid, acrylamide, dimethyl acrylamide, vinyl alcohol and the like. Representative examples of suitable bulk materials include, but are not limited to, polymacon, tefilcon, methafilcon, deltafilcon, bufilcon, phemfilcon, ocufilcon, focofilcon, etafilcon, hefilcon, vifilcon, tetrafilcon, perfilcon, droxifilcon, dimefilcon, isofilcon, mafilcon, nelfilcon, atlafilcon and the like. Examples of other suitable bulk materials include balafilcon A, hilafilcon A, alphafilcon A, bilafilcon B and the like.

In another embodiment, an ophthalmic device includes a device which is formed from materials which are amphiphilic segmented copolymers containing at least one hydrophobic segment and at least one hydrophilic segment which are linked through a bond or a bridge member.

It is particularly useful to employ biocompatible materials herein including both soft and rigid materials commonly used for ophthalmic lenses, including contact lenses. In general, non-hydrogel materials are hydrophobic polymeric materials that do not contain water in their equilibrium state. Typical non-hydrogel materials comprise silicone acrylics, such as those formed from a bulky silicone monomer (e.g., tris(trimethylsiloxy)silylpropyl methacrylate, commonly known as "TRIS" monomer), methacrylate end-capped poly(dimethylsiloxane)prepolymer, or silicones having fluoroalkyl side groups (polysiloxanes are also commonly known as silicone polymers).

In another embodiment, an ophthalmic device includes a device which is a hydrogel. Hydrogels in general are a well-known class of materials that comprise hydrated, cross-linked polymeric systems containing water in an equilibrium state. Accordingly, hydrogels are copolymers prepared from hydrophilic monomers. In the case of silicone hydrogels, the hydrogel copolymers are generally prepared by polymerizing a mixture containing at least one device-forming silicone-containing monomer and at least one device-forming hydrophilic monomer. Either the silicone-containing monomer or the hydrophilic monomer can function as a cross-linking agent (a crosslinker being defined as a monomer having multiple polymerizable functionalities) or a separate crosslinker may be employed. Silicone hydrogels typically have a water content between about 10 to about 80 weight percent.

Representative examples of useful hydrophilic monomers include, but are not limited to, amides such as N,N-dimethylacrylamide and N,N-dimethylmethacrylamide; cyclic lactams such as N-vinyl-2-pyrrolidone; and (meth)acrylated poly(alkene glycols), such as poly(diethylene glycols) of varying chain length containing monomethacrylate or dimethacrylate end caps. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277, the disclosures of which are incorporated herein by reference. Other suitable hydrophilic monomers will be apparent to one skilled in the art. For example, 2-hydroxyethylmethacrylate (HEMA) is a well-known hydrophilic monomer that may be used in admixture with the aforementioned hydrophilic monomers.

The monomer mixtures may also include a second device-forming monomer including a copolymerizable group and a reactive functional group. The copolymerizable group is preferably an ethylenically unsaturated group, such that this device-forming monomer copolymerizes with the hydrophilic device-forming monomer and any other device-forming monomers in the initial device-forming monomer mixture. Additionally, the second monomer can include a reactive functional group that reacts with a complementary reactive group of the copolymer such as the reaction product of one or more polymerizable polyhydric alcohols and one or more polymerizable fluorine-containing monomers. In other words, after the device is formed by copolymerizing the device-forming monomer mixture, the reactive functional groups provided by the second device-forming monomers remain to react with a complementary reactive moiety of the copolymer.

In an embodiment, reactive groups of the second device-forming monomers include epoxide groups. Accordingly, second device-forming monomers are those that include both an ethylenically unsaturated group (that permits the monomer to copolymerize with the hydrophilic device-forming monomer) and the epoxide group (that does not react with the hydrophilic device-forming monomer but remains to react with a copolymer, e.g., the reaction product of one or more polymerizable polyhydric alcohols and one or more polymerizable fluorine-containing monomers). Suitable second device-forming monomers include, for example, glycidyl methacrylate, glycidyl acrylate, glycidyl vinylcarbonate, glycidyl vinylcarbamate, and 4-vinyl-1-cyclohexene-1,2-epoxide.

As mentioned, one class of ophthalmic device materials are silicone hydrogels. In this case, the initial device-forming monomer mixture further comprises a silicone-containing monomer. Applicable silicone-containing monomeric materials for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995. Specific examples of suitable materials for use herein include those disclosed in U.S. Pat. Nos. 5,310,779; 5,387,662; 5,449,729; 5,512,205; 5,610,252; 5,616,757; 5,708,094; 5,710,302; 5,714,557 and 5,908,906, the contents of which are incorporated by reference herein.

Representative examples of applicable silicone-containing monomers include bulky polysiloxanylalkyl(meth)

acrylic monomers. An example of a bulky polysiloxanylalkyl(meth)acrylic monomer is represented by the structure of Formula (I):

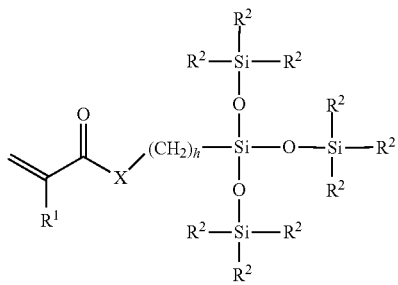
(I)

wherein X denotes —O— or —NR— wherein R denotes hydrogen or a $C_1$ to $C_4$ alkyl; 1e denotes hydrogen or methyl; each $R^2$ independently denotes a lower alkyl radical such as a $C_1$ to $C_4$ alkyl radical, a phenyl radical or a group represented by

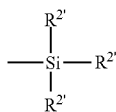

wherein each $R^{2'}$ independently denotes a lower alkyl radical such as a $C_1$ to $C_4$ alkyl radical, or a phenyl radical; and h is 1 to 10.

Examples of bulky monomers are methacryloxypropyl tris(trimethyl-siloxy)silane or tris(trimethylsiloxy)silylpropyl methacrylate, sometimes referred to as TRIS and tris (trimethylsiloxy)silylpropyl vinyl carbamate, sometimes referred to as TRIS-VC and the like.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, for example, silicone-containing vinyl carbonate or vinyl carbamate monomers such as, for example, 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy)silane]; 3-[tris(trimethyl siloxy)silyl]propyl vinyl carbamate; 3-[tris (trimethylsiloxy)silyl]propyl allyl carbamate; 3-[tris(trimethylsiloxy)silyl]propyl vinyl carbonate; t-butyl dimethylsiloxyethyl vinyl carbonate; trimethylsilylethyl vinyl carbonate; trimethylsilylmethyl vinyl carbonate and the like and mixtures thereof.

Another class of silicone-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacryates in Polyurethane-Polysiloxane Hydrogels," Journal of Applied Polymer Science, Vol. 60, 1193-1199 (1996). PCT Published Application No. WO 96/31792 discloses examples of such monomers, which disclosure is hereby incorporated by reference in its entirety. Further examples of silicone urethane monomers are represented by Formula (II) and (III):

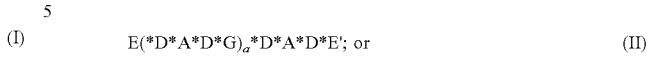

wherein:

D independently denotes an alkyl diradical, an alkyl cycloalkyl diradical, a cycloalkyl diradical, an aryl diradical or an alkylaryl diradical having 6 to about 30 carbon atoms;

G independently denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A independently denotes a divalent polymeric radical of Formula (IV):

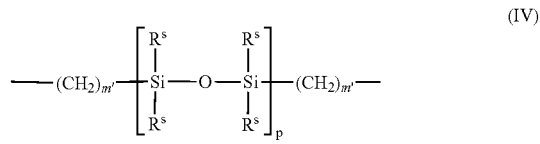
(IV)

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula (V):

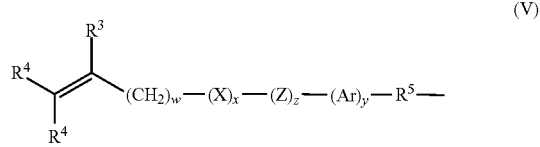
(V)

wherein: $R^3$ is hydrogen or methyl;

$R^4$ is hydrogen, an alkyl radical having 1 to 6 carbon atoms, or a —CO—Y—$R^6$ radical wherein Y is —O—, —S— or —NH—;

$R^5$ is a divalent alkylene radical having 1 to about 10 carbon atoms;

$R^6$ is a alkyl radical having 1 to about 12 carbon atoms;

X denotes —CO— or —OCO—;

Z denotes —O— or —NH—;

Ar denotes an aromatic radical having about 6 to about 30 carbon atoms;

w is 0 to 6; x is 0 or 1; y is 0 or 1; and z is 0 or 1.

In an embodiment, a silicone-containing urethane monomer is represented by Formula (VI):

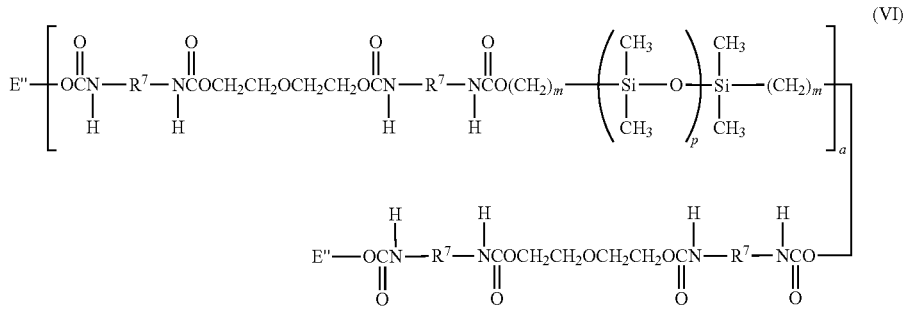

wherein m is at least 1 and is preferably 3 or 4, a is at least 1 and preferably is 1, p is a number which provides a moiety weight of about 400 to about 10,000 and is preferably at least about 30, $R^7$ is a diradical of a diisocyanate after removal of the isocyanate group, such as the diradical of isophorone diisocyanate, and each E" is a group represented by:

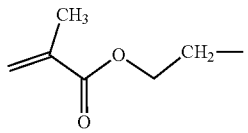

In another embodiment, a silicone hydrogel material comprises (in bulk, that is, in the monomer mixture that is copolymerized) about 5 to about 50 percent, or from about 10 to about 25 percent, by weight of one or more silicone macromonomers, about 5 to about 75 percent, or about 30 to about 60 percent, by weight of one or more polysiloxanyl-alkyl (meth)acrylic monomers, and about 10 to about 50 percent, or about 20 to about 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 discloses additional unsaturated groups, including acryloxy or methacryloxy. Fumarate-containing materials such as those disclosed in U.S. Pat. Nos. 5,310,779; 5,449,729 and 5,512,205 are also useful substrates in accordance with the invention. The silane macromonomer may be a silicon-containing vinyl carbonate or vinyl carbamate or a polyurethane-polysiloxane having one or more hard-soft-hard blocks and end-capped with a hydrophilic monomer.

In another embodiment, a class of silicon-containing monomers includes monomers of Formula (VII):

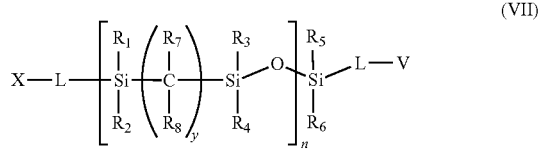

wherein X is the residue of a ring opening agent; L is the same or different and is a linker group or a bond; V is an ethylenically unsaturated polymerizable group; $R_1$, $R_2$, $R_3$, $R_4$, $R_5$, $R_6$ are independently H, alkyl, halo alkyl, cyclo alkyl, heterocyclo alkyl, alkenyl, halo alkenyl, or aromatic; $R_7$ and $R_8$ are independently H or alkyl wherein at least one of $R_7$ or $R_8$ is hydrogen; y is 2 to 7 and n is 1 to 100.

Ring opening agents are well known in the literature. Non-limiting examples of anionic ring opening agents include alkyl lithiums, alkoxides, trialkylsiloxylithium wherein the alkyl group may or may not contain halo atoms.

Linker groups can be any divalent radical or moiety and include substituted or unsubstituted alkyl, alkyl ether, alkenyls, alkenyl ethers, halo alkyls, substituted or unsubstituted siloxanes, and monomers capable of propagating ring opening.

Ethylenically unsaturated polymerizable groups are well known to those skilled in the art. Non-limiting examples of ethylenically unsaturated polymerizable groups would include acrylates, methacrylates, vinyl carbonates, O-vinyl carbamates, N-vinyl carbamates, acrylamides and methacrylamides.

In another embodiment, a class of silicone-containing monomers includes monomers of Formula (VIII):

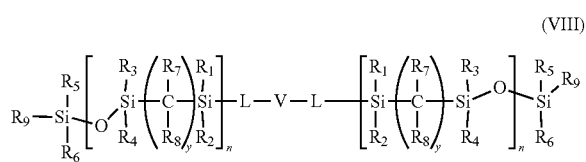

wherein L is the same or different and is a linker group or a bond; V is the same or different and is an ethylenically unsaturated polymerizable group; $R_1$, $R_2$, $R_3$, $R_4$, $R_5$, $R_6$ and $R_9$ are independently H, alkyl, halo alkyl, cyclo alkyl, heterocyclo alkyl, alkenyl, halo alkenyl, or aromatic; $R_7$ and $R_8$ are independently H or alkyl wherein at least one of $R_7$ or $R_8$ is hydrogen; y is 2-7 and n is 1-100.

In another embodiment, a class of silicone-containing monomers includes monomers of Formulas (IX) and (X):

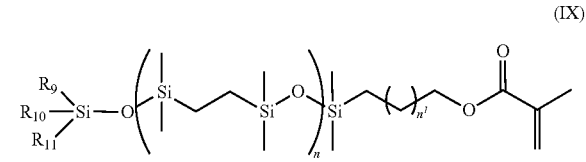

wherein $R_9$, $R_{10}$ and $R_{11}$ are independently H, alkyl, haloalkyl or other substituted alkyl groups; n is as defined above and $n^1$ is 0-10; and, (X)

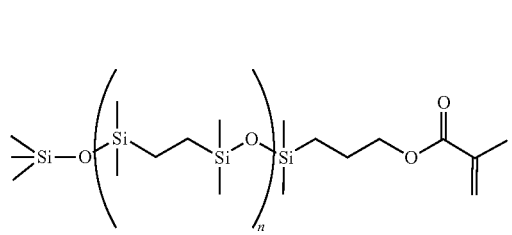

wherein n is 1 to 100, or n is 2 to 80, or n is 3 to 20, or n is 5 to 15.

In another embodiment, a class of silicon-containing monomers includes monomers of Formulas (XI)-(XV):

(M1-EDS6-TMS) (XI)

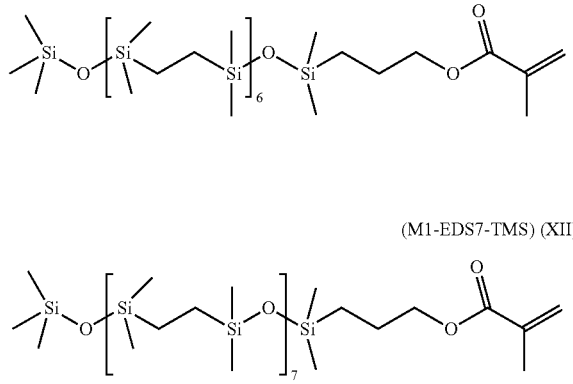

(M1-EDS7-TMS) (XII)

(M1-EDS9-TMS) (XIII)

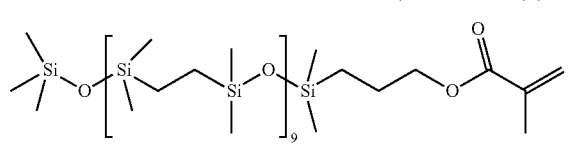

(M1-EDS12-TMS) (XIV)

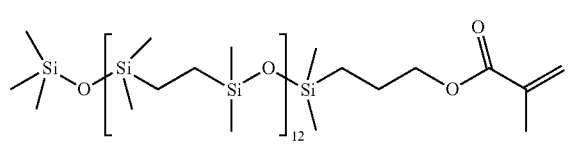

(M1-EDS15-TMS) (XV)

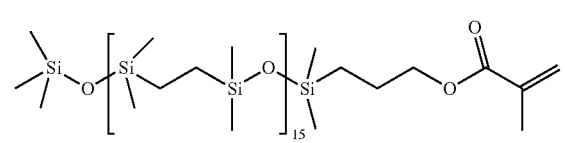

In another embodiment, a class of silicone-containing monomers includes monomers of Formulas (XVI)-(XVIII):

(XVI)

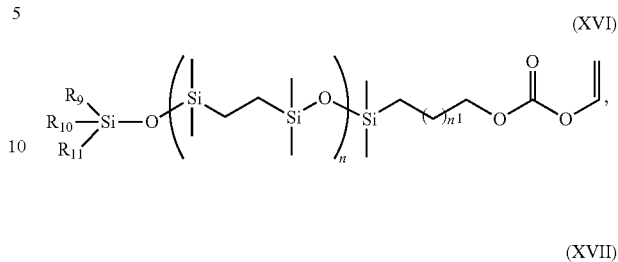

(XVII)

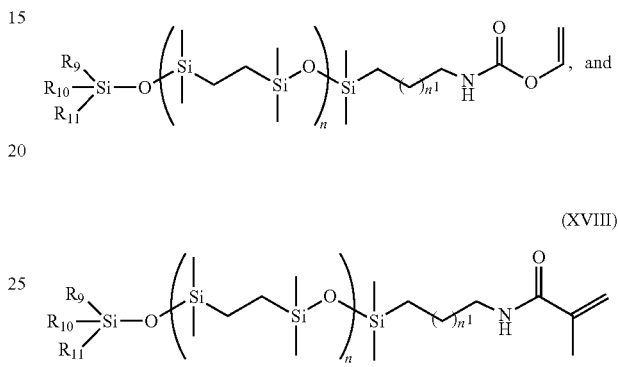

(XVIII)

wherein $R_9$, $R_{10}$ and $R_{11}$ are independently H, alkyl, haloalkyl or other substituted alkyl groups and n and $n^1$ are as defined above.

In another embodiment, a class of silicone-containing monomers includes monomers of Formulas (XIX)-(XXI):

(XIX)

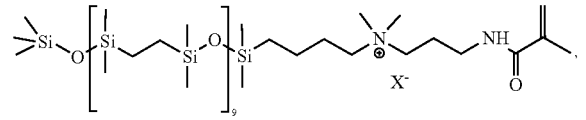

(XX)

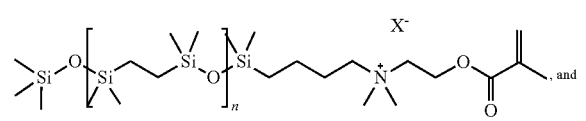

(XXI)

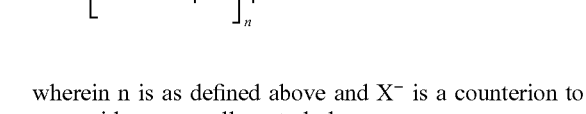

wherein n is as defined above and $X^-$ is a counterion to provide an overall neutral charge.

Counterions capable of providing an overall neutral charge are well known to those of ordinary skill in the art and would include, for example, halide ions.

In another embodiment, a class of silicone-containing monomers includes monomers of Formula (XXII):

(M1-EDS7-D37-TMS)

(XXII)

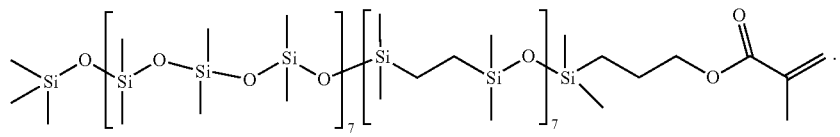

Another class of representative silicone-containing monomers includes fluorinated monomers. Such monomers have been used in the formation of fluorosilicone hydrogels to reduce the accumulation of deposits on contact lenses made therefrom, as disclosed in, for example, U.S. Pat. Nos. 4,954,587; 5,010,141 and 5,079,319. Also, the use of silicone-containing monomers having certain fluorinated side groups, i.e., —($CF_2$)—H, have been found to improve compatibility between the hydrophilic and silicone-containing monomeric units. See, e.g., U.S. Pat. Nos. 5,321,108 and 5,387,662.

The above silicone materials are merely exemplary, and other materials for use as substrates that have been disclosed in various publications and are being continuously developed for use in contact lenses and other ophthalmic devices can also be used. For example, an ophthalmic device can be formed from at least a cationic monomer such as cationic silicone-containing monomer or cationic fluorinated silicone-containing monomers.

Ophthalmic devices such as contact lenses can be manufactured employing various conventional techniques, to yield a shaped article having the desired posterior and anterior lens surfaces. Spincasting methods are disclosed in U.S. Pat. Nos. 3,408,429 and 3,660,545; and static casting methods are disclosed in U.S. Pat. Nos. 4,113,224, 4,197,266 and 5,271,876. Curing of the monomeric mixture may be followed by a machining operation in order to provide a contact lens having a desired final configuration. As an example, U.S. Pat. No. 4,555,732 discloses a process in which an excess of a monomeric mixture is cured by spincasting in a mold to form a shaped article having an anterior lens surface and a relatively large thickness. The posterior surface of the cured spincast article is subsequently lathe cut to provide a contact lens having the desired thickness and posterior lens surface. Further machining operations may follow the lathe cutting of the lens surface, for example, edge-finishing operations.

As one skilled in the art will readily appreciate, ophthalmic device surface functional groups of the ophthalmic device may be inherently present at the surface of the device. However, if the ophthalmic device contains too few or no functional groups, the surface of the device can be modified by known techniques or conventional functionalization with groups such as —OH, —$NH_2$ or —$CO_2H$. Suitable ophthalmic device surface functional groups of the biomedical device include a wide variety of groups well known to the skilled artisan. Representative examples of such functional groups include, but are not limited to, hydroxy groups, amino groups, carboxy groups, carbonyl groups, aldehyde groups, sulfonic acid groups, sulfonyl chloride groups, isocyanato groups, carboxy anhydride groups, lactone groups, azlactone groups, epoxy groups and groups being replaceable by amino or hydroxy groups, such as halo groups, or mixtures thereof. In an embodiment, the ophthalmic device surface functional groups of the ophthalmic device are amino groups and/or hydroxy groups.

Next, the resulting ophthalmic device such as a contact lens will be immersed in an aqueous packaging solution and stored in a packaging system according to illustrative embodiments described herein. Generally, a packaging system for the storage of an ophthalmic device includes at least a sealed container containing one or more unused ophthalmic devices immersed in an aqueous packaging solution. In an illustrative embodiment, the sealed container is a hermetically sealed blister-pack, in which a concave well containing an ophthalmic device such as a contact lens is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, and the like.

In an illustrative embodiment, the aqueous packaging solution for use in the packaging system disclosed herein will contain at least ectoine or an ophthalmologically acceptable ectoine derivative, e.g., hydroxyectoine. Ectoine is a natural substance which is obtained from microorganisms which live in extreme environments (e.g., salt lakes). These microorganisms form the natural substance ectoine in order to protect themselves from the extreme environmental factors prevailing there.

In an illustrative embodiment, the ectoine is L-ectoine ((S)-2-methyl-1,4,5,6-tetrahydropyrimidine-4-carboxylic acid). In an illustrative embodiment, ophthalmologically acceptable ectoine derivatives include, for example, hydroxyectoine ((4S,5S)-5-hydroxy-2-methyl-1,4,5,6-tetrahydropyrimidine-4-carboxylic acid), polyectoine, oliogomers thereof, salts, e.g. sodium- or potassium salts, of ectoine, esters which can be obtained by conversion of the 4-carboxy group with alcohols, in particular straight-chain or branched mono- or bivalent alcohols with 1 to 20 carbon atoms, and/or of the 5-hydroxy group with carboxylic acids, in particular straight-chain or branched-chain mono- or bivalent alkyl carboxylic acids with 2 to 20 carbon atoms, e.g., alkylmonocarboxylic acids, and also acid addition salts with inorganic or organic acids.

In an illustrative embodiment, the ectoine or ophthalmologically acceptable ectoine derivative is present in the aqueous packaging solution in an amount ranging from about 0.01 to about 10 weight percent, based on the total weight of the aqueous packaging solution. In another illustrative embodiment, the ectoine or an ophthalmologically acceptable ectoine derivative is present in the aqueous packaging solution in an amount ranging from about 0.1 to about 2 weight percent, based on the total weight of the aqueous packaging solution.

The aqueous packaging solution for use in the packaging systems disclosed herein can further contain one or more glycosaminoglycans (GAG) and/or one or more modified glycosaminoglycans. A GAG is one molecule with many alternating subunits. In general, GAGs are represented by the formula A-B-A-B-A-B, where A is uronic acid and B is an amino sugar that may or may not be either O- or N-sulfated, where the A and B units can be heterogeneous with respect to epimeric content or sulfation. Any natural or synthetic polymer containing uronic acid can be used. Other GAGs are sulfated at different sugars. There are many different types of GAGs having commonly understood structures such as, for example, chondroitin sulfate (e.g., chondroitin 4- and 6-sulfates), heparan, heparin sulfate, heparosan, dermatan, dermatan sulfate, hyaluronic acid or a salt thereof, e.g., sodium hyaluronate or potassium hyaluronate, keratan sulfate, and other disaccharides such as sucrose, lactulose, lactose, maltose, trehalose, cellobiose, mannobiose and chitobiose. Glycosaminoglycans can be purchased from Sigma, and many other biochemical suppliers such as HTL Biotechnology (France). In an illustrative embodiment, the GAG is hyaluronic acid. In another illustrative embodiment, the GAG is chondroitin sulfate.

In an illustrative embodiment, a GAG for use herein can have a weight average molecular weight ranging from about 10,000 to about 3,000,000 Daltons (Da) in which the lower limit is from about 10,000, about 20,000, about 30,000, about 40,000, about 50,000, about 60,000, about 70,000, about 80,000, about 90,000, or about 100,000 Da, and the upper limit is about 200,000, about 300,000, about 400,000, about 500,000, about 600,000, about 700,000, about 800,000, about 900,000, about 1,000,000, or about up to 2,800,000 Da, where any of the lower limits can be combined with any of the upper limits. In an illustrative embodiment, a GAG for use herein can have a weight average molecular weight ranging from about 1,000,000 to about 3,000,000 Da.

Hyaluronic acid is a well-known, naturally occurring, water soluble biodegradable polymer composed of two alternatively linked sugars, D-glucuronic acid and N-acetyl-glucosamine, linked via alternating β-(1,4) and β-(1,3) glycosidic bonds. Hyaluronic acid is a non-sulfated GAG. The polymer is hydrophilic and highly viscous in aqueous solution at relatively low solute concentrations. It often occurs naturally as the sodium salt, sodium hyaluronate. Methods of preparing commercially available hyaluronan and salts thereof are well known. Hyaluronan can be purchased from Seikagaku Company, Clear Solutions Biotech, Inc., Pharmacia Inc., Sigma Inc., HTL Biotechnology, Contipro and Bloomage Biotechnology Corporation, and many other suppliers. Hyaluronic acid has repeating units of the structure represented by the following formula:

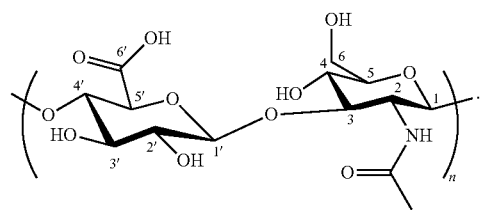

Accordingly, the repeating units in hyaluronic acid can be as follows:

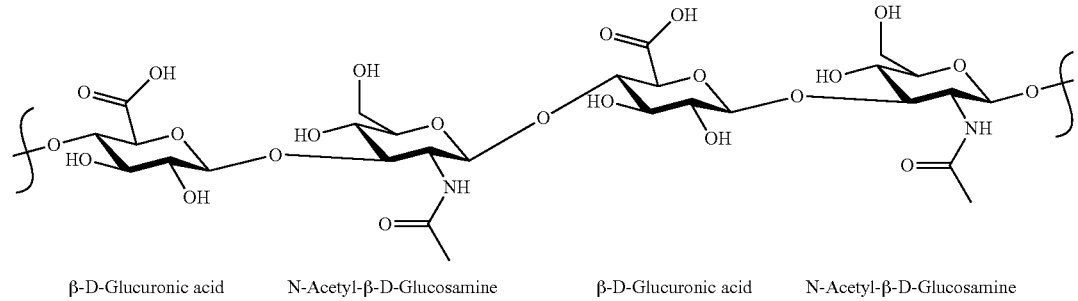

β-D-Glucuronic acid    N-Acetyl-β-D-Glucosamine    β-D-Glucuronic acid    N-Acetyl-β-D-Glucosamine In general, hyaluronic acid or a salt thereof can have from about 2 to about 1,500,000 disaccharide units. In an embodiment, hyaluronic acid or a salt thereof can have a weight average molecular weight ranging from about 10,000 to about 3,000,000 Da in which the lower limit is from about 10,000, about 20,000, about 30,000, about 40,000, about 50,000, about 60,000, about 70,000, about 80,000, about 90,000, or about 100,000 Da, and the upper limit is about 200,000, about 300,000, about 400,000, about 500,000, about 600,000, about 700,000, about 800,000, about 900,000, about 1,000,000, or about up to 2,800,000 Da, where any of the lower limits can be combined with any of the upper limits.

Chondroitin sulfate is a linear sulfated polysaccharide composed of repeating β-D-glucuronic acid (GlcA) and N-acetyl-β-D-galactosamine (GalNAc) units arranged in the sequence by GlcA-β(1,3)-GalNAc-β(1,4) glycosidic bonds. In an embodiment, chondroitin sulfate has one or more repeating units of the structure represented by the following formula:

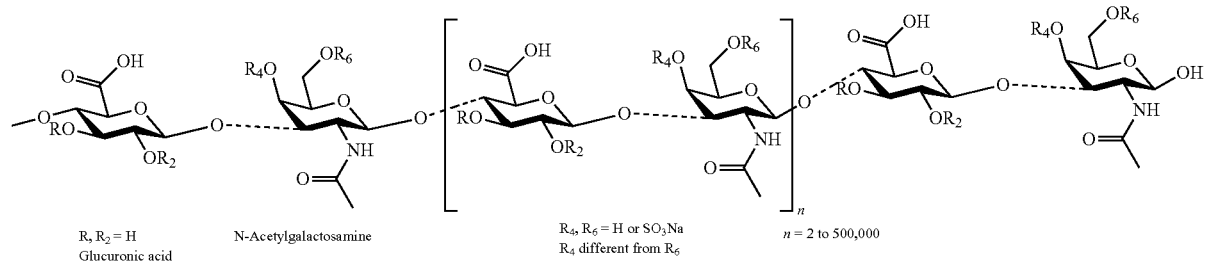

R, R₂ = H
Glucuronic acid

N-Acetylgalactosamine

R₄, R₆ = H or SO₃Na
R₄ different from R₆ n = 2 to 500,000

In an illustrative embodiment, chondroitin sulfate has repeating units of the structure represented by the following formula:

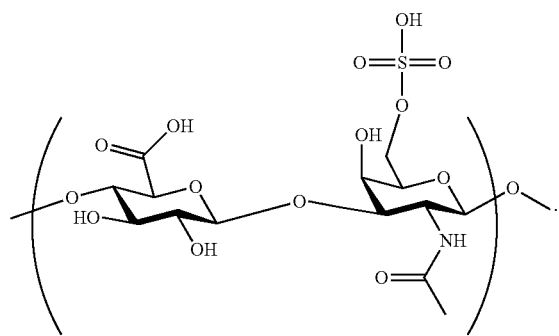

In general, chondroitin sulfate can have from about 2 to about 1,500,000 repeating units. In an embodiment, chondroitin sulfate can have a weight average molecular weight ranging from about 10,000 to about 3,000,000 Da in which the lower limit is from about 5,000, 10,000, about 20,000, about 30,000, about 40,000, about 50,000, about 60,000, about 70,000, about 80,000, about 90,000, or about 100,000 Da, and the upper limit is about 200,000, about 300,000, about 400,000, about 500,000, about 600,000, about 700,000, about 800,000, about 900,000, about 1,000,000, or about 3,000,000 Da where any of the lower limits can be combined with any of the upper limits or any of the upper limits can be combined with any of the upper limits.

In an illustrative embodiment, dermatan sulfate has repeating units of the structure represented by the following formula:

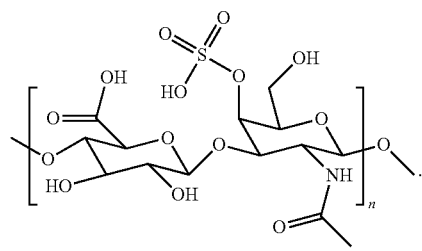

In general, dermatan sulfate can have from about 2 to about 1,500,000 repeating units. In an embodiment, dermatan sulfate can have a weight average molecular weight ranging from about 1,000 to about 2,000,000 Da in which the lower limit is from about 1,000, 5,000, 10,000, about 20,000, about 30,000, about 40,000, about 50,000, about 60,000, about 70,000, about 80,000, about 90,000, or about 100,000 Da, and the upper limit is about 200,000, about 300,000, about 400,000, about 500,000, about 600,000, about 700,000, about 800,000, about 900,000, about 1,000,000, or about 2,000,000 Da where any of the lower limits can be combined with any of the upper limits or any of the upper limits can be combined with any of the upper limits.

In an illustrative embodiment, heparin and heparin sulfate has repeating units of the structure represented by the following formula:

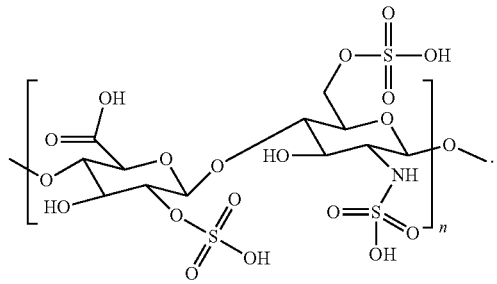

In general, heparin and heparin sulfate can have from about 2 to about 1,500,000 repeating units. In an embodiment, heparin and heparin sulfate can have a weight average molecular weight ranging from about 1,000 to about 3,000,000 Da in which the lower limit is from about 1,000, 5,000, 10,000, about 20,000, about 30,000, about 40,000, about 50,000, about 60,000, about 70,000, about 80,000, about 90,000, or about 100,000 Da, and the upper limit is about 40,000, 100,000, 200,000, about 300,000, about 400,000, about 500,000, about 600,000, about 700,000, about 800,000, about 900,000, about 1,000,000, or about 3,000,000 Da where any of the lower limits can be combined with any of the upper limits or any of the upper limits can be combined with any of the upper limits.

In an illustrative embodiment, keratan sulfate has repeating units of the structure represented by the following formula:

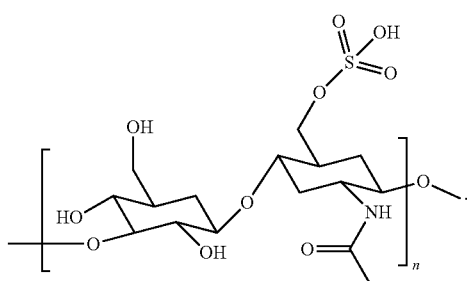

In general, keratan sulfate can have from about 2 to about 1,500,000 repeating units. In an embodiment, keratan sulfate can have a weight average molecular weight ranging from about 10,000 to about 3,000,000 Da in which the lower limit is from about 5,000, 10,000, about 20,000, about 30,000, about 40,000, about 50,000, about 60,000, about 70,000, about 80,000, about 90,000, or about 100,000 Da, and the upper limit is about 100,000, 200,000, about 300,000, about 400,000, about 500,000, about 550,000, 600,000, about 700,000, about 800,000, about 900,000, about 1,000,000, or about 3,000,000 Da where any of the lower limits can be combined with any of the upper limits or any of the upper limits can be combined with any of the upper limits.

The one or more GAG's can be further derivatized to form a modified GAG. For example, in an illustrative embodiment, the one or more GAGs can be a crosslinked polymeric network comprising a reaction product of a first GAG, a second GAG, and one or more crosslinking agents, wherein the first glycosaminoglycan is different than the second glycosaminoglycan. Any of the foregoing GAGs can be used in forming the crosslinked polymeric network. In an embodiment, the first GAG is hyaluronic acid or a salt thereof and the second GAG is chondroitin sulfate.

The reaction product includes one or more crosslinking agents, e.g., to crosslink the first glycosaminoglycan with the second glycosaminoglycan. The crosslinking agents for use herein can be any suitable crosslinking agent known in the art. In general, a suitable crosslinking agent is, for example, a crosslinking agent having complimentary functional groups to the first glycosaminoglycan such as hyaluronic acid and to the second glycosaminoglycan such as chondroitin sulfate. In an embodiment, a suitable crosslinking agent includes, for example, a bi- or polyfunctional crosslinking agent. The bi- or polyfunctional crosslinking agent connects the first glycosaminoglycan with the second glycosaminoglycan. In addition, the bi- or polyfunctional crosslinking agent further acts as a spacer between the first glycosaminoglycan and the second glycosaminoglycan. In general, the bi- or polyfunctional crosslinking agent comprises two or more functional groups capable of reacting with functional groups of the first glycosaminoglycan such as hyaluronic acid and the second glycosaminoglycan such as chondroitin sulfate, resulting in the formation of covalent bonds.

Suitable bi- or polyfunctional crosslinking agents include, for example, divinyl sulfone, diepoxides, multiepoxides, dihydrazides, dihydric alcohols, polyhydric alcohols, polyhydric thiols, anhydrides, carbodiimdes, polycarboxylic acids, carboxymethyl thiols, cysteine, and cysteine-like amino acids and the like. In an embodiment, a bi- or polyfunctional crosslinking agent is a bis- or polyepoxide, such as diglycidyl ether derivatives. According to an embodiment, the bi- or polyfunctional epoxide crosslinking agent comprises two or more glycidyl ether functional groups. The glycidyl ether functional groups react with primary hydroxyl groups of the hyaluronic acid and the chondroitin sulfate, resulting in the formation of ether bonds. In an embodiment, suitable bis- or polyfunctional crosslinking agents include, for example, 1,4-butanediol diglycidyl ether (BDDE), 1,2-bis(2,3-epoxypropoxy)ethylene (EGDGE), ethylene glycol diglycidyl ether (EGDE), 1,2-ethanediol diglycidyl ether (EDDE), diepoxyoctane, 1,6-hexanediol diglycidyl ether, polypropylene glycol diglycidyl ether, polytetramethylene glycol diglycidyl ether, neopentyl glycol diglycidyl ether, polyglycerol polyglycidyl ester, diglycerol polyglycidyl ether, glycerol polyglycidyl ether, trimethylolpropane polyglycidyl ether, pentaerythritol polyglyglycidyl ether, sorbitol polyglycidyl ether, 1,2,7,8-diepoxyoctane, 1,3-butadiene diepoxide, pentaerythritol tetraglycidyl ether, polyepoxides and the like.

Suitable dihydrazide crosslinking agents include, for example, succinic acid dihydrazide, glutaric acid dihydrazide, adipic acid dihydrazide, pimelic acid dihydrazide, suberic acid dihydrazide, azalaic acid dihydrazide, sebacic acid dihydrazide, undecanedioic acid dihydrazide, dodecanedioic acid dihydrazide, brassylic acid dihydrazide, tetradecanedioic acid dihydrazide, pentadecanedioic acid dihydrazide, thapsic acid dihydrazide, octadecanedioic acid dihydrazide and the like.

Suitable dihydric alcohol crosslinking agents include, for example, ethylene glycol, propylene glycol, butylene glycol diethylene glycol, dipropylene glycol, neopentyl glycol, 1,3-propanediol, hexylene glycol, pentylene glycol, heptylene glycol, octylene glycol and the like. Suitable polyhydric alcohol crosslinking agents include, for example glycerin, pentaerythrite, xylitol, galactitol and the like. Suitable carbodiimide crosslinking agents include, for example, a compound of formula X—N=C=N—X, wherein each X independently is a $C_1$ to $C_6$ alkyl optionally substituted with 1-2 dialkylamino groups, or is a $C_5$ to $C_6$ cycloalkyl group, such as 1-ethyl-3-(3-dimethylaminopropyl) carbodimide hydrochloride, and cyclohexyl carbodiimide. Suitable anhydride crosslinking agents include, for example, methacrylic anhydride, octeyl succinic anhydride and the like. In an embodiment, a suitable crosslinking agent is an aldehyde crosslinking agent such as, for example, formaldehyde, gluteraldehyde, gluraraldehyde and the like. In an embodiment, a suitable crosslinking agent includes, for example, an acid chloride, n-hydroxysuccinimide, polyethylene glycol diacrylates, polyethylene glycol diamines, ureas, diisocyanates and the like.

The crosslinked polymeric network disclosed herein can be obtained by forming a solution of the first glycosaminoglycan and second glycosaminoglycan, and adding the foregoing one or more crosslinking agents. The solution is stirred for a suitable time sufficient to crosslink at least the first glycosaminoglycan with the second glycosaminoglycan. In an embodiment, crosslinking between the glycosaminoglycans can take place between 1° C. and about 99° C. over a time period of about 2 hours to about 24 hours.

The solution can contain a suitable solvent such as, for example, water, crown-ethers, dimethyl sulphoxide (DMSO), dimethyl formamide (DMF) and other aprotic solvents. In general, the amount of the first glycosaminoglycan can range from about 0.010 to about 50 wt. %, based on the total weight of the solution. In an embodiment, the amount of the first glycosaminoglycan can range from about 0.1 to about 5 wt. %, based on the total weight of the solution. In an embodiment, the amount of the second glycosaminoglycan can range from about 0.01 to about 50 wt. %, based on the total weight of the solution. In an embodiment, the amount of the second glycosaminoglycan can range from about 0.1 to about 5 wt. %, based on the total weight of the solution. The crosslinking agent can be added to the solution in an amount ranging from about 0.05 to about 10 wt. %, based on the total weight of the solution.

It will be readily understood and appreciated by those skilled in the art that the reaction product constitutes a complex mixture of compounds including, for example, the first glycosaminoglycan crosslinked with the second glycosaminoglycan, the first glycosaminoglycan crosslinked with the first glycosaminoglycan, the second glycosaminoglycan crosslinked with the second glycosaminoglycan, unreacted first glycosaminoglycan and unreacted second glycosaminoglycan. For example, in an illustrative embodiment, a first glycosaminoglycan crosslinked with a second glycosaminoglycan can have a weight average molecular weight ranging from about 20,000 to about 6,000,000 Da in which the lower limit is from about 20,000, about 30,000, about 40,000, about 50,000, about 60,000, about 70,000, about 80,000, about 90,000, or about 100,000 Da, and the upper limit is about 200,000, about 300,000, about 400,000, about 500,000, about 600,000, about 700,000, about 800,000, about 900,000, about 1,000,000, about 2,000,000, about 3,000,000, about 4,000,000, about 5,000,000 or up to about 6,000,000 Da where any of the lower limits can be combined with any of the upper limits. It is not necessary to isolate one or more specific components of the reaction product mixture. Indeed, the reaction product mixture can be employed as is.

In an embodiment, the crosslinked polymeric network disclosed herein can be further crosslinked with one or more of the same or different third glycosaminoglycans. In general, the one or more third glycosaminoglycans can be any of the glycosaminoglycans discussed hereinabove. In an embodiment, the one or more third glycosaminoglycans are hyaluronic acid. In an embodiment, the one or more third glycosaminoglycans are chondroitin sulfate. In an embodiment, the one or more third glycosaminoglycans include hyaluronic acid and chondroitin sulfate.

The crosslinking agent for crosslinking the one or more of the same or different third glycosaminoglycans with the foregoing crosslinked polymeric network can be any of the crosslinking agents discussed above. As one skilled in the art will understand, the crosslinking agent can the same crosslinking agent or a different crosslinking agent as the crosslinking agent used in the foregoing reaction product.

In general, the crosslinked polymeric network disclosed can be further crosslinked with one or more of the same or different third glycosaminoglycans in substantially the same manner as discussed above.

In another illustrative embodiment, a modified glycosaminoglycan can be obtained by further reacting the one or more GAGs with one or more phospholipids and optionally one or more crosslinking agents to form glycophospholipid polymers or crosslinked glycophospholipid polymeric networks. Suitable phospholipids for reacting with the one or more GAGs comprise, for example, phosphorylcholine, phosphorylhistidine, phosphorylproline, phosphoryl serine, α-phosphatidylcholine, α-phosphatidylethanolamine, α-phosphatidyl-L-serine, α-phosphatidylinositol, α-phosphatidic acid, α-phosphatidyl-DL-glycerol, α-lysophosphatidylcholine, sn-glycero-3-phosphatidylcholine (GPC) (also choline alfoscerate) derived from soybean phosphatidylcholine sphingomyelin, and cardiolipin. The phospholipids described herein are either commercially available or can be made by techniques well known in the art, see, e.g., Park et al., "Facile Syntheses of L-α-Glycerophosphorylcholine", Bull. Korean Chem. Soc. 2010, Vol. 31, No. pp. 9 2689-2691.

In an embodiment, a phosphorylcholine-containing phospholipid comprises a zwitterionic group as follow:

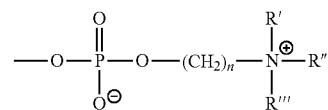

wherein n is an integer of 1 to 5 and R', R" and R'" independently of each other are a $C_1$ to $C_8$ alkyl group, a $C_1$ to $C_8$ hydroxyalkyl group or a hetero atom-containing group such as histidine and proline. As one skilled in the art will readily appreciate, the foregoing phosphorylcholine-containing phospholipid will further include one or more reactive groups capable of reacting with the one or more GAGs, e.g., hydroxyl-containing groups, epoxide-containing groups, amine-containing groups, aldehyde-containing groups, thiol-containing groups, carboxylic acid-containing groups, cyano-containing groups, halogen-containing groups, etc. Representative examples of suitable phosphorylcholine phospholipids having the foregoing zwitterionic group include, but are not limited to, glycerylphosphorylcholine, ethanaminium, 2·[[hydroxy·2·oxiranylmethoxy]phosphinyl)oxy)·N,N,N·trimethyl, inner salt, and hydroxyethylphophorylcholine.

The term "hydroxyl-containing group" should be understood to mean any group which contains a hydroxyl moiety. Representative examples of hydroxyl-containing groups for use herein include, by way of example, a hydroxy group attached directly to the rest of the molecule, i.e., —OH, or one or more hydroxy-containing groups attached to the rest of the molecule via a linking group, e.g., an alkyl, cycloalkyl, cycloalkylalkyl, cycloalkenyl, aryl or an arylalkyl group and the like.

The term "epoxide-containing group" should be understood to mean any group which contains an epoxide moiety. Representative examples of epoxide-containing groups for use herein include, by way of example, alkylene oxides and in particular lower alkylene oxides such as ethylene oxide, propylene oxide, butylene oxide, alcohol epoxides such as glycidol, and epihalohydrins such as epichlorohydrin, epibromohydrin, epiiodohydrin, 1,2-epoxy-4-chlorobutane, 1,2-epoxy-4-bromobutane, 1,2-epoxy-4-iodobutane, 2,3-epoxy-4-chlorobutane, 2,3-epoxy-4-bromobutane, 2,3-epoxy-4-iodobutane, 2,3-epoxy-5-chloropentane, 2,3-epoxy-5-bromopentane, 1,2-epoxy-5-chloropentane, etc.; epoxy compounds such as 2,2-bis(p-1,2-epoxypropoxyphenyl)-propane, 1,4-bis(1,2-epoxypropoxy)benzene, N,N'-bis(2,3-epoxypropyl)piperazine, etc.

The term "amine-containing group" should be understood to mean any group which contains an amine moiety. Representative examples of amine-containing groups for use herein include, by way of example, an alky or arylamine group such as an amine of the general formula —$R^1NR^2R^3$ wherein $R^1$ is a $C_2$ to $C_{30}$ alkylene, arylene, or cycloalkylene and $R^2$ and $R^3$ are independently $C_1$ to $C_{30}$ hydrocarbons such as, for example, alkyl groups, aryl groups, or cycloalkyl groups as defined herein.

The term "aldehyde-containing group" should be understood to mean any group which contains an aldehyde moiety.

Representative examples of aldehyde-containing groups for use herein include, by way of example, an aldehyde group attached directly to the rest of the molecule, i.e., —CHO, or one or more aldehyde groups attached to the rest of the molecule via a linking group, e.g., an alkylene, cycloalkyl, cycloalkylalkylene, cycloalkenyl, aryl or an arylalkylene group and the like.

The term "thiol-containing group" should be understood to mean any group which contains a thiol moiety. Representative examples of thiol-containing groups for use herein include, by way of example, a thiol group attached directly to the rest of the molecule, i.e., —SH, or one or more thiol groups attached to the rest of the molecule via a linking group, e.g., an alkylene, cycloalkyl, cycloalkylalkylene, cycloalkenyl, aryl or an arylalkylene group and the like.

The term "carboxylic acid-containing group" should be understood to mean any group which contains a carboxylic acid moiety. Representative examples of carboxylic acid-containing groups for use herein include, by way of example, a carboxylic acid group attached directly to the rest of the molecule, i.e., —COOH, or one or more carboxylic acid groups attached to the rest of the molecule via a linking group, e.g., an alkylene, cycloalkyl, cycloalkylalkylene, cycloalkenyl, aryl or an arylalkylene group and the like.

The term "cyano-containing group" should be understood to mean any group which contains a cyano moiety. Representative examples of cyano-containing groups for use herein include, by way of example, a cyano group attached directly to the rest of the molecule, i.e., —CN, or one or more cyano groups attached to the rest of the molecule via a linking group, e.g., an alkylene, cycloalkyl, cycloalkylalkylene, cycloalkenyl, aryl or an arylalkylene group and the like.

The term "halogen-containing group" should be understood to mean any group which contains a halogen moiety. Representative examples of halogen-containing groups for use herein include, by way of example, a halogen group attached directly to the rest of the molecule, i.e., F, Cl, B, I and the like, or one or more halogen groups attached to the rest of the molecule via a linking group, e.g., an alkylene, cycloalkyl, cycloalkylalkylene, cycloalkenyl, aryl or an arylalkylene group and the like.

Representative examples of alkyl groups for use herein include, by way of example, a straight or branched hydrocarbon chain radical containing carbon and hydrogen atoms of from 1 to about 18 carbon atoms with or without unsaturation, to the rest of the molecule, e.g., methyl, ethyl, n-propyl, l-methylethyl (isopropyl), n-butyl, n-pentyl, etc., and the like.

Representative examples of alkylene groups for use herein include, by way of example, a straight or branched alkyl chain radical containing carbon and hydrogen atoms of from 1 to about 30 carbon atoms or from 1 to about 6 carbon atoms with or without unsaturation, to the rest of the molecule, e.g., methylene, ethylene, and the like.

Representative examples of cycloalkyl groups for use herein include, by way of example, a substituted or unsubstituted non-aromatic mono or multicyclic ring system of about 3 to about 18 carbon atoms such as, for example, cyclopropyl, cyclobutyl, cyclopentyl, cyclohexyl, perhydronapththyl, adamantyl and norbornyl groups bridged cyclic group or sprirobicyclic groups, e.g., sprio-(4,4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 3 to about 18 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 18 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 25 carbon atoms such as, for example, phenyl, naphthyl, tetrahydronapthyl, indenyl, biphenyl and the like, optionally containing one or more heteroatoms, e.g., O and N, and the like.

Representative examples of arylalkylene groups for use herein include, by way of example, a substituted or unsubstituted aryl group as defined above directly bonded to an alkylene group as defined above, e.g., —$CH_2C_6H_5$, —$C_2H_5C_6H_5$ and the like, wherein the aryl group can optionally contain one or more heteroatoms, e.g., O and N, and the like.

The phospholipids for use herein are either commercially available or can be prepared by methods known in the art. For example, ethanaminium, 2·[[hydroxy-2-oxiranylmethoxy]phosphinyl)oxy)-N,N,N·trimethyl, inner salt can be prepared according to a method described in Example 11 in the J. Org. Chemistry, 67, 194-199 (2002) or as in U.S. Pat. No. 7,674,782, the contents of which are incorporated by reference herein. In addition, hydroxyethylphosphorylcholine can be prepared according to Journal of the American Chemical Society, 130(23), 7357-7363 (2008), the contents of which are incorporated by reference herein, and is also commercially available from Shanghai Chemhere Co., Ltd. (Shanghai, Hong Kong).

In an illustrative embodiment, the reaction product of the one or more GAGs and the one or more phospholipids includes one or more crosslinking agents, e.g., to crosslink the one or more GAGs with the one or more phospholipids and form a crosslinked glycophospholipid polymeric network. The crosslinking agents for use herein can be any of the crosslinking agent discussed above for crosslinking a first GAG with a second GAG.

The glycophospholipid polymeric network disclosed herein can be obtained by forming a solution of the one or more GAGs and the one or more phospholipids, and optionally adding the one or more crosslinking agents when forming a crosslinked polymeric network. The solution is stirred for a suitable time sufficient to react and/or crosslink the one or more GAGs and the one or more phospholipids. In an embodiment, the reaction between the one or more GAGs and the one or more phospholipids can take place between 1° C. and about 99° C., over a time period of about 2 hours to about 36 hours.

The solution can contain suitable one or more solvents such as, for example, water, crown-ethers, dimethyl sulphoxide (DMSO), dimethyl formamide (DMF) and other aprotic solvents.

In general, the amount of the one or more GAGs in the solution can range from about 0.010 to about 50 wt. %, based on the total weight of the solution. In an illustrative embodiment, the amount of the one or more GAGs in the solution can range from about 0.1 to about 5 wt. %, based on the total weight of the solution. In an illustrative embodiment, the amount of the one or more phospholipids in the solution can range from about 0.01 to about 50 wt. %, based on the total weight of the solution. In an illustrative embodiment, the amount of the one or more phospholipids in the solution can range from about 0.1 to about 5 wt. %, based on the total weight of the solution. The crosslinking agent can be added to the solution in an amount ranging from about 0.05 to about 20 wt. %, based on the total weight of the solution.

It will be readily understood and appreciated by those skilled in the art that the reaction product constitutes a complex mixture of compounds. For example, a reaction product of one or more GAGs, one or more phospholipids, and one or more crosslinking agents can include, by way of example, the polymer obtained from the reaction between one or more GAGs and the one or more phospholipids, the GAG crosslinked with the phospholipid, the GAG crosslinked with the GAG, the phospholipid crosslinked with the phospholipid, unreacted GAG and unreacted phospholipid. In an illustrative embodiment, a GAG crosslinked with a phospholipid can have a weight average molecular weight ranging from about 20,000 to about 6,000,000 Da in which the lower limit is from about 20,000, about 30,000, about 40,000, about 50,000, about 60,000, about 70,000, about 80,000, about 90,000, or about 100,000 Da, and the upper limit is about 200,000, about 300,000, about 400,000, about 500,000, about 600,000, about 700,000, about 800,000, about 900,000, about 1,000,000, about 2,000,000, about 3,000,000, about 4,000,000, about 5,000,000 or up to about 6,000,000 Da where any of the lower limits can be combined with any of the upper limits. It is not necessary to isolate one or more specific components of the reaction product mixture. Indeed, the reaction product mixture can be employed as is.

In yet another illustrative embodiment, a modified glycosaminoglycan can include one or more GAGs having a polymer backbone and one or more side chains comprising a polyalkylene glycol-containing residue grafted onto the polymer backbone to form a grafted glycosaminoglycan polymer. In general, the GAGs discussed above will have a reactive functional group in the polymer backbone for grafting a polymer comprising polyalkylene glycol chains and at least one reactive end group or a salt thereof. Suitable reactive functional groups in the polymer backbone include carboxylate-containing groups, hydroxyl-containing groups, silicone hydride groups, sulfur-containing groups such as thiols and other groups including polymerizable functionalities such as allylic, vinylic, acrylate, methacylate, methacrylamide etc. In addition, the sugar rings of the GAGs can be opened to form aldehydes for further functionalization. The GAGs for use herein can have a weight average molecular weight as discussed above.

The polyalkylene glycol-containing residue grafted onto a reactive functional group in the polymer backbone of the GAG is derived from a polymer comprising polyalkylene glycol chains and at least one reactive end group or a salt thereof (e.g., HCl). The polyalkylene glycol chains can range from 2 to 10,000 subunits or from 2 to 5000 subunits. In an embodiment, the polyalkylene glycol chains comprise a structure: $-((CH_2)_a-O)_b-$ where "a" is from 2 to 6 or from 2 to 4 and "b" is from 2 to 10,000 or from 2 to 5000. In an illustrative embodiment, a polyalkylene glycol is one or more of polyethylene glycol chains such as (e.g., $-(CH_2CH_2O)_b-$) (i.e., PEG), polypropylene glycol chains (e.g., $-(CH_2CH_2CH_2O)_b-$), polybutylene glycol chains (e.g., $-(CH_2CH_2CH_2CH_2O)_b-$), ethylene oxide-propylene oxide chains, and ethylene oxide-butylene oxide chains.

The at least one reactive end group of the polymer comprising polyalkylene glycol chains includes a reactive functional group capable of grafting on to the reactive functional group in the polymer backbone of the GAG. Suitable reactive functional groups include, for example, a halogen, amino groups, aldehyde groups, carboxylic acid groups, alcohol groups, thiol groups, hydrazide groups, glycidyl groups, etc. These groups are attached to the polymeric compound by way of a linker group "X". Examples of reactive functional groups include $-X-PDMS-NH_2$ where PDMS is polydimethylsiloxane having a number molecular weight ranging from about 100 to about 150,000 Da, $-X-OH$, $-X-NH_2$, $-X-SH$, and $-X-C(O)-R'$ where R' is hydrogen or an organic hydrocarbyl moiety comprised of 1 to 20 carbon atoms such as a lower alkyl group (e.g., methyl, ethyl, propyl, etc.) or benzyl.

Suitable linker groups "X" for attaching the reactive functional end group to the polymer include, for example, any of the following: $-C(O)-$, $-N-C(O)-NH-CH_2-$, $-N-C(O)-NH-CH_2-CH_2-$, $-CH_2-$, $-CH_2-CH_2-$, $-CH_2-CH_2-CH_2-$, $-CH_2-CH_2-CH_2-CH_2-$, $-CH_2-O-CH_2-$, $-CH_2-O-CH_2-CH_2-$, $-CH_2-CH_2-CH_2-O-CH_2-$, $-C(O)-NH-CH_2-$, $-C(O)-NH-CH_2-CH_2-$, $-CH_2-C(O)-NH-CH_2-$, $-CH_2-CH_2-C(O)-NH-$, $-C(O)-NH-CH_2-CH_2-CH_2-$, $-CH_2-C(O)-NH-CH_2-CH_2-$, $-CH_2-CH_2-C(O)-NH-CH_2-$, $-C(O)-NH-CH_2-CH_2-CH_2-CH_2-$, $-CH_2-C(O)-NH-CH_2-CH_2-CH_2-$, $-CH_2-CH_2-C(O)-NH-CH_2-CH_2-$, $-CH_2-CH_2-CH_2-C(O)-NH-CH_2-$, $-CH_2-CH_2-CH_2-(Si-O-Si)_n-O-Si-CH_2-CH_2-CH_2-$ where n=3 to 100 and combinations of two or more of any of the foregoing.

The other end group can be either an inert end-capping group or a reactive end-group. An inert end-capping group is one that does not readily undergo chemical transformation under typical synthetic reaction conditions. A reactive end group can be used for further cross-linking. Suitable end-capping groups include, for example, an alkoxy group, a hydroxyl group, a thiol group, an amine group and an ethylenically polymerizable group such as, for example, an acrylate or methacrylate group. An alkoxy group is represented by the general formula $-OR$, where R is an organic moiety comprised of 1-20 carbon atoms such as a lower alkyl group (e.g., methyl or ethyl) or benzyl. R, however, may be saturated or unsaturated, and includes aryl, heteroaryl, cyclo, heterocyclo, and substituted forms of any of the foregoing. For example, an end-capped PEG can comprise the structure $RO-(CH_2CH_2O)_n-$ where R is as defined above. In an illustrative embodiment, suitable end groups include, by way of example, $-OCH_3$, $-OCH_2CH_3$, $-OCH_2(C_6H_5)$, $-NH_2$, $-OH$, and $-SH$.

The polymers comprising polyalkylene glycol chains and at least one reactive end group or a salt thereof for use herein include polymers having a variety of molecular weights, structures or geometries (e.g., branched, linear, and the like). In an illustrative embodiment, the weight average molecular weight of a polymer comprising polyalkylene glycol chains and at least one reactive end group or a salt thereof may range from about 100 Da to about 10,000 Da. For example, in an illustrative embodiment, the weight average molecular weight of a polymer comprising polyalkylene glycol chains and at least one reactive end group or a salt thereof can be greater than about 100 Daltons, or greater than about 250 Da, or greater than about 500 Da, or greater than about 750 Da, or greater than about 1,000 Da, or greater than about 2,000 Da, or greater than about 5,000 Da, or greater than about 7,500 Da. In another illustrative embodiment, the weight average molecular weight of a polymer comprising polyalkylene glycol chains and at least one reactive end group or a salt thereof can be less than about 10,000 Da, or less than about 7,500 Da, or less than about 5,000 Da, or less than about 2,000 Da, or less than about 1,000 Da, or less than about 750 Da, or less than about 600 Da. As one skilled in the art can appreciate, any molecular weight between those listed above can be used.

The foregoing polymers are either commercially available from various sources such as BroadPharm, Sigma, JenKem, and Advanced Polymer Materials Inc. or can be prepared according to methods well known in the art.

In an illustrative embodiment, a polymer comprising polyalkylene glycol chains and at least one reactive end group or a salt thereof is a polymer or a salt thereof having the following structure:

$$Z—(((CH_2)_a—O)_b)_c—Y$$

wherein Z is an end-capped group, Y is a reactive functional group, a is from 2 to 6, b is from 2 to 10,000 and c is 1 or 2.

Z is an end-capped (or end-capping) group which can be an inert group or a reactive group present on a terminus of the polymeric compound such as a polyethylene glycol (PEG) polymer. Suitable end-capped groups include any of those discussed above. Y is a reactive functional group capable of grafting on to the reactive functional group in the polymer backbone of the GAG. Suitable reactive functional groups include any of those discussed above. Suitable linker groups "X" for attaching the reactive functional group any of those discussed above.

The polymers may be derived from a polyalkylene glycol. In general, a polyalkylene glycol comprises the following structure: —((CH$_2$)$_a$—O)$_b$— where "a" is from 2 to 6 or from 2 to 4 and "b" is from 2 to 10,000 or from 2 to 5000. In an illustrative embodiment, a polyalkylene glycol is one or more of a polyethylene glycol (e.g., —(CH$_2$CH$_2$O)$_b$—), a polypropylene glycol (e.g., —(CH$_2$CH$_2$CH$_2$O)$_b$—) a polybutylene glycol (e.g., —(CH$_2$CH$_2$CH$_2$CH$_2$O)$_b$—), ethylene oxide-propylene oxide, and ethylene oxide-butylene oxide. The polyalkylene glycols for use herein include polyalkylene glycols having a variety of molecular weights, structures or geometries (e.g., branched, linear, and the like) as discussed above.

In an embodiment, representative examples of such polymers for use herein include any of the following:

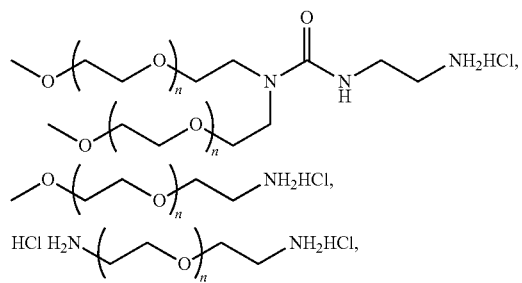

wherein n is from 2 to 10,000.

The grafted glycosaminoglycan polymers disclosed herein can be obtained by grafting the reactive functionality of the one or more polymers comprising polyalkylene glycol chains onto the reactive functionality in the polymer backbone of the glycosaminoglycan. For example, in an illustrative embodiment, an amine reactive end group of the polymer comprising polyalkylene glycol chains can be grafted onto a carboxylic acid group in the polymer backbone of the glycosaminoglycan. The graft polymerization reaction can obtain a degree of grafting, i.e., the number of sidechains in the polymer backbone containing the polyalkylene glycol-containing residue, ranging from about 5 to about 100%. In an illustrative embodiment, the degree of grafting can range from about 10 to about 90%. In an illustrative embodiment, the degree of grafting can range from about 20 to about 80%.

In an illustrative embodiment, a glycosaminoglycan can be added to the reaction mixture in an amount ranging from about 0.05 wt. % to about 10 wt. %, based on the total weight of the reaction mixture. In an illustrative embodiment, a glycosaminoglycan can be added to the reaction mixture in an amount ranging from about 0.5 wt. % to about 5 wt. %, based on the total weight of the reaction mixture.

In an embodiment, a polymer comprising polyalkylene glycol chains can be added to the reaction mixture in an amount ranging from about 0.01 wt. % to about 20 wt. %, based on the total weight of the reaction mixture. In an illustrative embodiment, a polymer comprising polyalkylene glycol chains can be added to the reaction mixture in an amount ranging from about 0.10 wt. % to about 0.5 wt. %, based on the total weight of the reaction mixture.

The grafting reaction is ordinarily carried out in the presence of a catalyst system. In some embodiments, the catalyst system is a carbodiimide catalyst system such as, for example, 1-ethyl-3-(3-dimethylaminopropyl)carbodiimide (EDC). In some embodiments, a co-catalyst is used with the carbodiimide catalyst system. Suitable co-catalysts include, for example, hydroxybenzotriazole (HOBt), N-hydroxysuccinimide (NHS) and sulfo-N-hydroxysuccinimide (Sulfo-NHS). In some embodiments, the catalyst system includes EDC/NHS. In an embodiment, the EDC is added to the reaction mixture in an amount ranging from about 0.01 wt. % to about 20 wt. %, based on the total weight of the reaction mixture. In an embodiment, the NHS is added to the reaction mixture in an amount ranging from about 0.01 wt. % to about 20 wt. %, based on the total weight of the reaction mixture.

In an illustrative embodiment, the grafting reaction can be carried out by reacting the glycosaminoglycan with the polymer under suitable grafting conditions using a catalyst system such as EDC/NHS or EDC/HOBt coupling at a pH of about 6.8 with about 1 to about 5 weight percent dissolved solids in water to form random copolymers or block copolymers.

In another embodiment, the grafting reaction is carried out by reacting the glycosaminoglycan with monomers capable of forming a polymer comprising polyalkylene glycol chains and at least one reactive end group or a salt thereof in-situ. For example, the reaction can be carried out by first forming a solution containing at least the glycosaminoglycan and cocatalyst system. Next, the glycosaminoglycan is activated by adding an activator to the solution. A suitable activator includes, for example, one or more epoxyamines. Epoxyamines are molecules that generally include both at least one amine moiety (e.g., a primary, secondary, tertiary, or quaternary amine) and at least one epoxide moiety. The epoxyamine compound can be a monoepoxyamine compound and or a polyepoxyamine compound, i.e., an epoxyamine containing one or more amine groups and one or more epoxide groups. In an embodiment, a suitable epoxyamine compound is one in which the amine moiety is linked to the epoxide moiety by way of a $C_1$ to $C_{30}$ alkylene group. Suitable epoxyamine compounds include, for example, epoxyethylamine, epoxypropylamine, epoxybutylamine, epoxyamyl amine and the like. The activation reaction can be carried out at a suitable temperature and for a time period to react the activator with the glycosaminoglycan, e.g., at room temperature, and a time period ranging from about 10 hours to about 48 hours. In an embodiment, an epoxyamine can be added to the reaction mixture in an amount ranging from about 0.01 to about 50 wt. %, based on the total weight of the reaction mixture.

After the activator has been reacted with the glycosaminoglycan, the monomers capable of forming in-situ a polymer comprising polyalkylene glycol chains and at least one reactive end group or a salt thereof are added to the reaction mixture. In an embodiment, the monomers include a polyol and an epoxy alcohol. Suitable polyols include, for example one or more diols. Representative diols include, by way of example, a $C_2$ to $C_{12}$ diol such as ethylene glycol, propylene glycol, 1,3-propanediol, 1,2-butanediol, 1,4-butanediol, 2-methyl-1,3-propanediol, poloxamer 407 and the like. The epoxyalcohol compound can be a monoepoxyalcohol compound and or a polyepoxyalcohol compound, i.e., an epoxyalcohol containing one or more alcohol groups and one or more epoxide groups. In an embodiment, a suitable epoxyalcohol compound is one in which the alcohol moiety is linked to the epoxide moiety by way of a $C_1$ to $C_{30}$ alkylene and or alkyne group. Suitable epoxyalcohol compounds include, for example, glycidyl alcohol, 3-oxiranyl-2-Propen-1-ol, 3-(2-oxiranyl)2-propen-1-ol, 1-(2,3-dihydroxypropyl) 4-(2-oxiranylmethyl) ester of 2-butenedioic acid, and a 1-(2-hydroxyethyl) 2-(2-oxiranylmethyl) ester of 1,2-benzenedicarboxylic acid.

In general, the polyol and epoxyalcohol can be added sequentially or simultaneously to the reaction mixture. In an embodiment, the polyol is added to the reaction mixture and reacted with the activated glycosaminoglycan, followed by the polyol to form the polyalkylene glycol-containing residue. The reaction can be carried out at a suitable temperature and for a time period for the completion of the reaction to maximize the yield of the product polyalkylene glycol residue onto the polymer backbone of the glycosaminoglycan, e.g., at room temperature and a time period ranging from about 10 hours to about 48 hours. In an embodiment, a polyol can be added to the reaction mixture in an amount ranging from about 0.01 to about 50 wt. %, and an epoxyalcohol can be added to the reaction mixture in an amount ranging from about 0.01 to about 50 wt. %, based on the total weight of the reaction mixture.

The resulting grafted glycosaminoglycan polymer can be a random copolymer or a block copolymer. In an illustrative embodiment, a grafted glycosaminoglycan polymer disclosed herein can have a weight average molecular weight ranging from about 20,000 to about 6,000,000 Da in which the lower limit is from about 20,000, about 30,000, about 40,000, about 50,000, about 60,000, about 70,000, about 80,000, about 90,000, or about 100,000 Da, and the upper limit is about 200,000, about 300,000, about 400,000, about 500,000, about 600,000, about 700,000, about 800,000, about 900,000, about 1,000,000, about 2,000,000, about 3,000,000, about 4,000,000, about 5,000,000 or up to about 6,000,000 Da.

In another embodiment, a crosslinked polymer network can be formed by either reacting the foregoing grafted glycosaminoglycan polymers with one or more crosslinking agents, or adding one or more crosslinking agents to the grafting reaction mixture. The crosslinking agents for use herein can be any of the crosslinking agents discussed above such as, for example, a bi- or polyfunctional crosslinking agent comprises two or more functional groups capable of reacting with functional groups of the grafted glycosaminoglycan polymers resulting in the formation of covalent bonds.

In an embodiment, a crosslinked polymeric network described in exemplary embodiments herein can be obtained by forming a solution of the one or more grafted glycosaminoglycan polymers and adding one or more of the foregoing crosslinking agents. In an embodiment, a crosslinked polymeric network described in exemplary embodiments herein can be obtained by adding one or more of the foregoing crosslinking agents to the grafting solution of the one or more glycosaminoglycan polymers and one or more polymers. The solution is stirred for a suitable time sufficient to crosslink the reaction mixture. In an embodiment, the crosslinking can take place between 1° C. and about 99° C. over a time period of about 2 hours to about 48 hours.

The solution can contain a suitable solvent such as, for example, water, crown-ethers, dimethyl sulphoxide (DMSO), dimethyl formamide (DMF) and other aprotic solvents. The pH of the solution can be adjusted if necessary by adding, for example, a hydroxide such as sodium hydroxide. In general, the crosslinking agent can be added to the solution in an amount ranging from about 0.01 wt. % to about 10 wt. %, based on the total weight of the solution. When crosslinking the grafted glycosaminoglycan polymer, the amount of the grafted glycosaminoglycan polymer can range from about 0.010 wt. % to about 50 wt. %, based on the total weight of the solution. In an embodiment, the amount of the grafted glycosaminoglycan polymer can range from about 0.01 wt. % to about 5 wt. %, based on the total weight of the solution.

In an embodiment, one or more glycosaminoglycans can be added to the reaction of the grafted glycosaminoglycan polymers and one or more crosslinking agents to form a crosslinked polymeric network, i.e., to crosslink the grafted glycosaminoglycan polymers with the one or more glycosaminoglycans. In general, the one or more glycosaminoglycans can be any of the glycosaminoglycans discussed hereinabove. In an embodiment, the one or more glycosaminoglycans are hyaluronic acid or a salt thereof. In an embodiment, the one or more glycosaminoglycans are chondroitin sulfate. In an embodiment, the one or more glycosaminoglycans include hyaluronic acid or a salt thereof and chondroitin sulfate. In an illustrative embodiment, the amount of the one or more glycosaminoglycans can range from about 0.010 wt. % to about 50 wt. %, based on the total weight of the solution. In an embodiment, the amount of the one or more glycosaminoglycans can range from about 0.01 wt. % to about 5 wt. %, based on the total weight of the solution.

The one or more crosslinking agents will have complimentary functional groups to the grafted glycosaminoglycan polymer and to the glycosaminoglycan. For example, a suitable crosslinking agent such as a bi- or polyfunctional crosslinking agent connects the grafted glycosaminoglycan polymer with the glycosaminoglycan, and further acts as a spacer between the grafted glycosaminoglycan polymer and the glycosaminoglycan.

It will be readily understood and appreciated by those skilled in the art that the reaction product constitutes a complex mixture of compounds including, for example, the grafted glycosaminoglycan polymer crosslinked with the glycosaminoglycan, the grafted glycosaminoglycan polymer crosslinked with the grafted glycosaminoglycan polymer, the glycosaminoglycan crosslinked with the glycosaminoglycan, unreacted grafted glycosaminoglycan polymer and unreacted glycosaminoglycan. For example, in an illustrative embodiment, a grafted glycosaminoglycan polymer crosslinked with a glycosaminoglycan can have a weight average molecular weight ranging from about 20,000 to about 6,000,000 Da in which the lower limit is from about 20,000, about 30,000, about 40,000, about 50,000, about 60,000, about 70,000, about 80,000, about 90,000, or about 100,000 Da, and the upper limit is about 200,000, about 300,000, about 400,000, about 500,000, about 600,000, about 700,000, about 800,000, about 900,000, about 1,000,000, about 2,000,000, about 3,000,000, about 4,000,000, about 5,000,000 or up to about 6,000,000 Da where any of the lower limits can be combined with any of the upper limits. It is not necessary to isolate one or more specific components of the reaction product mixture. Indeed, the reaction product mixture can be employed as is. If necessary, any excess crosslinker can be removed by dialysis or precipitation in ethanol.

In an illustrative embodiment, the one or more GAGs or modified GAGs as discussed above are present in the aqueous packaging solution in an amount ranging from about 0.01 to about 1 weight percent, based on the total weight of the aqueous packaging solution. In another illustrative embodiment, the one or more GAGs or modified GAGs as discussed above are present in the aqueous packaging solution in an amount ranging from about 0.01 to about 0.1 weight percent, based on the total weight of the aqueous packaging solution.

The packaging solutions disclosed herein are physiologically compatible. Specifically, the solution must be "ophthalmically safe" for use with a lens such as a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and includes materials, and amounts thereof, that are non-cytotoxic according to ISO standards and U.S. Food & Drug Administration (FDA) regulations.

The packaging solution should also be sterile in that the absence of microbial contaminants in the product prior to release must be statistically demonstrated to the degree necessary for such products. The liquid media useful in the present invention are selected to have no substantial detrimental effect on the lens being treated or cared for and to allow or even facilitate the present lens treatment or treatments. In an embodiment, the liquid media is aqueous-based. A particularly useful aqueous liquid medium is that derived from saline, for example, a conventional saline solution or a conventional buffered saline solution.

The pH of the packaging solutions should be maintained within the range of about 6 to about 9, or from about 6.5 to about 7.8. Suitable buffers may be added, such as boric acid, sodium borate, potassium citrate, citric acid, sodium bicarbonate, TRIS and various mixed phosphate buffers (including combinations of $Na_2HPO_4$, $NaH_2PO_4$ and $KH_2PO_4$) and mixtures thereof. In an illustrative embodiment, a suitable buffer is tris(hydroxymethyl)aminomethane (2-amino-2-(hydroxymethyl)propane-1,3-diol), (also known as tromethamine, and commonly referred to as tris, tris buffer, tris base or TRIZMA, TRIZMA buffer or TRIZMA base) or a salt thereof such as TRIZMA HCL. In an illustrative embodiment, the first component is tris(hydroxymethyl)aminomethane in the base form. In an illustrative embodiment, a suitable buffer is a borate buffer, containing one or more of boric acid, sodium borate, potassium tetraborate, potassium metaborate or mixtures of the same. Combinations of buffers are contemplated herein.

Generally, buffers will be used in amounts ranging from about 0.05 to about 2.5 weight percent, based on the total weight of the aqueous packaging solution. In an embodiment, buffers will be used in amounts ranging from about 0.1 to about 1.5 weight percent, based on the total weight of the aqueous packaging solution.

Typically, the aqueous packaging solutions are also adjusted with tonicity agents, to approximate the osmotic pressure of normal lacrimal fluids which is equivalent to a 0.9 percent solution of sodium chloride or 2.5 percent of glycerol solution. The aqueous packaging solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Suitable tonicity adjusting agents include, for example, sodium and potassium chloride, dextrose, calcium and magnesium chloride and the like and mixtures thereof. These tonicity adjusting agents are typically used individually in amounts ranging from about 0.01 to about 2.5% w/v. In an embodiment, the tonicity adjusting agents are used in amounts ranging from about 0.2 to about 1.5% w/v. The tonicity agent will be employed in an amount to provide a final effective osmotic value of at least about 150 mOsm/kg. In an embodiment, the tonicity adjusting agents are used in an amount to provide a final effective osmotic value of from about 150 to about 400 mOsm/kg. In an embodiment, the tonicity adjusting agents are used in an amount to provide a final effective osmotic value of from about 150 to about 350 mOsm/kg. In an embodiment, the tonicity adjusting agents are used in an amount to provide a final effective osmotic value of from about 160 to about 220 mOsm/kg.

If desired, one or more additional components can be included in the packaging solution. Such additional components are chosen to impart or provide at least one beneficial or desired property to the aqueous packaging solution. In general, the additional components may be selected from components which are conventionally used in one or more ophthalmic device care compositions. Suitable additional components include, for example, comfort agents, cleaning agents, wetting agents, nutrient agents, sequestering agents, viscosity builders, contact lens conditioning agents, antioxidants, and the like and mixtures thereof. These additional components may each be included in the packaging solutions in an amount effective to impart or provide the beneficial or desired property to the packaging solutions. For example, such additional components may be included in the packaging solutions in amounts similar to the amounts of such components used in other, e.g., conventional, contact lens care products.

In an illustrative embodiment, the aqueous packaging solution will further contain one or more comfort agents to provide additional lubricating and moisturizing characteristics to the aqueous packaging solutions. In an embodiment, a suitable comfort agent is one or more poloxamer comfort agents. A representative example of a suitable poloxamer comfort agent is a poloxamer block copolymer. One specific class of poloxamer block copolymers are those available under the trademark Pluronic (BASF Wyandotte Corp., Wyandotte, Mich.). Poloxamers include Pluronics and reverse Pluronics. Pluronics are a series of ABA block copolymers composed of poly(ethylene oxide)-poly(propylene oxide)-poly(ethylene oxide) blocks as generally represented in Formula (XXIII):

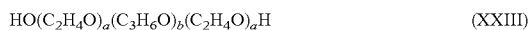

$$HO(C_2H_4O)_a(C_3H_6O)_b(C_2H_4O)_aH \qquad (XXIII)$$

wherein a is independently at least 1 and b is at least 1.

Reverse Pluronics are a series of BAB block copolymers, respectively composed of poly(propylene oxide)-poly(ethylene oxide)-poly(propylene oxide) blocks as generally represented in Formula (XXIV):

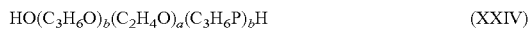

$$HO(C_3H_6O)_b(C_2H_4O)_a(C_3H_6P)_bH \qquad (XXIV)$$

wherein a is at least 1 and b is independently at least 1. The poly(ethylene oxide), PEO, blocks are hydrophilic, whereas the poly(propylene oxide), PPO, blocks are hydrophobic in nature. The poloxamers in each series have varying ratios of PEO and PPO which ultimately determines the hydrophilic-lipophilic balance (HLB) of the material, i.e., the varying HLB values are based upon the varying values of a and b, a representing the number of hydrophilic poly(ethylene oxide) units (PEO) being present in the molecule and b representing the number of hydrophobic poly(propylene oxide) units (PPO) being present in the molecule. In an embodiment, the poloxamer will have an HLB ranging from about 5 to about 24. In an embodiment, the poloxamer will have an HLB ranging from about 1 to about 5.

Poloxamers and reverse poloxamers have terminal hydroxyl groups that can be terminal functionalized. An example of a terminal functionalized poloxamer and as discussed herein is poloxamer dimethacrylate (e.g., Pluronic® F127 dimethacrylate) as disclosed in U.S. Patent Application Publication No. 2003/0044468 and U.S. Pat. No. 9,309,357. Other examples include glycidyl-terminated copolymers of polyethylene glycol and polypropylene glycol as disclosed in U.S. Pat. No. 6,517,933.

The poloxamer is functionalized to provide the desired reactivity at the end terminal of the molecule. The functionality can be varied and is determined based upon the intended use of the functionalized PEO- and PPO-containing block copolymers. That is, the PEO- and PPO-containing block copolymers are reacted to provide end terminal functionality that is complementary with the intended device forming monomeric mixture. The term block copolymer as used herein shall be understood to mean a poloxamer as having two or more blocks in their polymeric backbone(s).

In an embodiment, a suitable comfort agent is one or more polyol comfort agents. Suitable polyols for use herein have the formula R"(OH)$_y$ where R" is a hydrocarbon radical and y is an integer representing the number of hydroxy radicals and has a value of from 2 to 6. The polyols may contain less than about 12 carbon atoms. Representative examples of polyol comfort agents include glycerol, propylene glycol, erythritol, and the like.

In an embodiment, a suitable comfort agent is one or more poloxamine comfort agents. While the poloxamers and reverse poloxamers are considered to be difunctional molecules (based on the terminal hydroxyl groups), the poloxamines are in a tetrafunctional form, i.e., the molecules are tetrafunctional block copolymers terminating in primary hydroxyl groups and linked by a central diamine. One specific class of poloxamine block copolymers are those available under the trademark Tetronic (BASF). Poloxamines include Tetronic and reverse Tetronics. Poloxamines have the following general structure of Formula (XXVI):

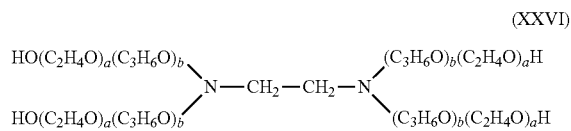

(XXVI)

wherein a is independently at least 1 and b is independently at least 1.

The poloxamine is functionalized to provide the desired reactivity at the end terminal of the molecule. The functionality can be varied and is determined based upon the intended use of the functionalized PEO- and PPO-containing block copolymers. That is, the PEO- and PPO-containing block copolymers are reacted to provide end terminal functionality that is complementary with the intended device forming monomeric mixture. The term block copolymer as used herein shall be understood to mean a poloxamine as having two or more blocks in their polymeric backbone(s).

In an embodiment, a suitable comfort agent includes water soluble natural gums, cellulose-derived polymers and the like. Useful natural gums include guar gum, gum tragacanth and the like. Suitable cellulose-derived comfort components include, for example, cellulose-derived polymers, such as hydroxypropyl cellulose, hydroxypropylmethyl cellulose, carboxymethyl cellulose, methyl cellulose, hydroxyethyl cellulose and the like.

In an embodiment, a suitable comfort agent can include, for example, polyacrylic acid (PAA)-containing comfort agents such as, for example, PAA-g-amine, PAA-g-lactose, PAA-co-amine and the like. Another suitable comfort agent is PDMA-co-mPEG.

Combinations of any of the foregoing comfort agents are contemplated herein.

In general, the one or more comfort agents are present in the aqueous packaging solution in an amount ranging from about 0.1 to about 5 weight percent, based on the total weight of the aqueous packaging solution. In an illustrative embodiment, the one or more comfort agents are present in the aqueous packaging solution in an amount ranging from about 0.1 to about 1 weight percent, based on the total weight of the aqueous packaging solution.

Suitable sequestering agents include, for example, disodium ethylene diamine tetraacetate, alkali metal hexametaphosphate, citric acid, sodium citrate and the like and mixtures thereof.

Suitable viscosity builders include, for example, hydroxyethyl cellulose, hydroxymethyl cellulose, polyvinyl pyrrolidone, polyvinyl alcohol and the like and mixtures thereof.

Suitable antioxidants include, for example, sodium metabisulfite, sodium thiosulfate, N-acetylcysteine, butylated hydroxyanisole, butylated hydroxytoluene and the like and mixtures thereof.

The method of packaging and storing an ophthalmic device such as a contact lens according to illustrative embodiments includes at least packaging an ophthalmic device immersed in the aqueous packaging solution disclosed herein. The method may include immersing the ophthalmic device in an aqueous packaging solution prior to delivery to the customer/wearer, directly following manufacture of the contact lens. Alternately, the packaging and storing in the packaging solution may occur at an intermediate point before delivery to the ultimate customer (wearer) but following manufacture and transportation of the lens in a dry state, wherein the dry lens is hydrated by immersing the lens in the packaging solution. Consequently, a package for delivery to a customer may include a sealed container containing one or more unused contact lenses immersed in an aqueous packaging solution according to the embodiments described herein.

In an illustrative embodiment, the steps leading to the packaging system disclosed herein include (1) molding an ophthalmic device in a mold comprising at least a first and second mold portion, (2) hydrating and cleaning the ophthalmic device in a container optionally comprising at least one of the mold portions, (3) introducing the aqueous packaging solution disclosed herein into the container with the ophthalmic device supported therein, and (4) sealing the container. In an illustrative embodiment, the method further includes the step of sterilizing the contents of the container. Sterilization may take place prior to, or most conveniently after, sealing of the container and may be affected by any suitable method known in the art, e.g., by autoclaving of the sealed container at temperatures of about 120° C. or higher.

The following examples are provided to enable one skilled in the art to practice the invention and are merely illustrative of the invention. The examples should not be read as limiting the scope of the invention as defined in the claims.

Example 1

An aqueous packaging solution is made by mixing the following components, listed in Table 1 at amounts per weight.

TABLE 1

| Ingredient | % w/w |
| --- | --- |
| Trizma HCl | 0.627 |
| Trizma Base | 0.116 |
| Sodium Chloride | 0.577 |
| Ectoine or ectoine derivative | 0.050-5.000 |
| Purified Water, USP | Q.S. to 100% w/w |

Example 2

An aqueous packaging solution is made by mixing the following components, listed in Table 2 at amounts per weight.

TABLE 2

| Ingredient | % w/w |
| --- | --- |
| Trizma HCl | 0.627 |
| Trizma Base | 0.116 |
| Sodium Chloride | 0.577 |
| Ectoineor ectoine derivative | 0.050-5.000 |
| Comfort Agents | 0.010-5.000 |
| Purified Water, USP | Q.S. to 100% w/w |

Example 3

An aqueous packaging solution is made by mixing the following components, listed in Table 3 at amounts per weight.

TABLE 3

| Ingredient | % w/w |
| --- | --- |
| Citric Acid, Anhydrous | 11.320 |
| Sodium Citrate | 62.220 |
| Sodium Chloride | 24.460 |
| Ectoine or ectoine derivative | 0.050-5.000 |
| Purified Water, USP | Q.S. to 100% w/w |

Example 4

An aqueous packaging solution is made by mixing the following components, listed in Table 4 at amounts per weight.

TABLE 4

| Ingredient | % w/w |
| --- | --- |
| Citric Acid, Anhydrous | 11.320 |
| Sodium Citrate | 62.220 |
| Sodium Chloride | 24.460 |
| Ectoine or ectoine derivative | 0.050-5.000 |
| Comfort Agents | 0.010-5.000 |
| Purified Water, USP | Q.S. to 100% w/w |

Example 5

An aqueous packaging solution is made by mixing the following components, listed in Table 5 at amounts per weight.

TABLE 5

| Ingredient | % w/w |
| --- | --- |
| 3-(N-Morpholino)propanesulfonic acid (MOPS) sodium salt | 0.560 |
| MOPS | 0.520 |
| Sodium Chloride | 0.630 |
| Ectoine or ectoine derivative | 0.050-5.000 |
| Purified Water, USP | Q.S. to 100% w/w |

Example 6

An aqueous packaging solution is made by mixing the following components, listed in Table 6 at amounts per weight.

TABLE 6

| Ingredient | % w/w |
| --- | --- |
| MOPS sodium salt | 0.560 |
| MOPS | 0.520 |
| Sodium Chloride | 0.630 |
| Ectoine or ectoine derivative | 0.050-5.000 |
| Comfort Agents | 0.010-5.000 |
| Purified Water, USP | Q.S. to 100% w/w |

Example 7

An aqueous packaging solution is made by mixing the following components, listed in Table 7 at amounts per weight.

TABLE 7

| Ingredient | % w/w |
| --- | --- |
| Monobasic sodium phosphate monohydrate | 0.015 |
| Dibasic sodium phosphate anhydrous | 0.065 |
| Sodium Chloride | 0.999 |
| Ectoine or ectoine derivative | 0.050-5.000 |
| Purified Water, USP | Q.S. to 100% w/w |

Example 8

An aqueous packaging solution is made by mixing the following components, listed in Table 8 at amounts per weight.

TABLE 8

| Ingredient | % w/w |
| --- | --- |
| Monobasic sodium phosphate monohydrate | 0.015 |
| Dibasic sodium phosphate anhydrous | 0.065 |
| Sodium Chloride | 0.999 |
| Ectoine or ectoine derivative | 0.050-5.000 |
| Comfort Agents | 0.010-5.000 |
| Purified Water, USP | Q.S. to 100% w/w |

Example 9

An aqueous packaging solution is made by mixing the following components, listed in Table 9 at amounts per weight.

TABLE 9

| Ingredient | % w/w |
| --- | --- |
| Sodium Borate | 0.610 |
| Boric Acid | 0.098 |
| Sodium Chloride | 0.886 |
| Ectoine or ectoine derivative | 0.050-5.000 |
| Purified Water, USP | Q.S. to 100% w/w |

Example 10

An aqueous packaging solution is made by mixing the following components, listed in Table 10 at amounts per weight.

TABLE 10

| Ingredient | % w/w |
| --- | --- |
| Sodium Borate | 0.610 |
| Boric Acid | 0.098 |
| Sodium Chloride | 0.886 |
| Ectoine or ectoine derivative | 0.050-5.000 |
| Comfort Agents | 0.010-5.000 |
| Purified Water, USP | Q.S. to 100% w/w |

Example 11

An aqueous packaging solution was made by mixing the following components, listed in Table 11 at amounts per weight.

TABLE 11

| Ingredient | % w/w |
| --- | --- |
| Monobasic sodium phosphate monohydrate | 0.015 |
| Dibasic sodium phosphate anhydrous | 0.065 |
| Sodium Chloride | 0.999 |
| Ectoine | 1.0 |
| Hyaluronic Acid-2 PEG | 0.04 |
| Purified Water, USP | Q.S. to 100% w/w |
| Hyaluronic Acid-2 PEG starting weight average molecular weight | 1.2 MDa |
| Pre-autoclave, weight average molecular weight of Hyaluronic Acid-2 PEG | 1.08 MDa |
| Post-autoclave, weight average molecular weight of Hyaluronic Acid-2 PEG | 0.59 MDa |

Example 12

An aqueous packaging solution was made by mixing the following components, listed in Table 12 at amounts per weight.

TABLE 12

| Ingredient | % w/w |
| --- | --- |
| Monobasic sodium phosphate monohydrate | 0.015 |
| Dibasic sodium phosphate anhydrous | 0.065 |
| Sodium Chloride | 0.999 |
| Ectoine | 1.0 |
| Hyaluronic Acid-2 PEG | 0.04 |
| Purified Water, USP | Q.S. to 100% w/w |
| Hyaluronic Acid-2 PEG starting weight average molecular weight | 2.3 MDa |
| Pre-autoclave, weight average molecular weight Hyaluronic Acid-2 PEG | 2.08 MDa |

TABLE 12-continued

| Ingredient | % w/w |
| --- | --- |
| Post-autoclave, weight average molecular weight of Hyaluranic Acid-2 PEG | 0.98 MDa |

Comparative Example A

An aqueous packaging solution was made by mixing the following components, listed in Table 13 at amounts per weight.

TABLE 13

| Ingredient | % w/w |
| --- | --- |
| Monobasic sodium phosphate monohydrate | 0.015 |
| Dibasic sodium phosphate anhydrous | 0.065 |
| Sodium Chloride | 0.999 |
| Ectoine | — |
| Hyaluranic Acid-2 PEG | 0.04 |
| Purified Water, USP | Q.S. to 100% w/w |
| Hyaluranic Acid-2 PEG starting weight average molecular weight | 1.2 MDa |
| Pre-autoclave, weight average molecular weight of Hyaluranic Acid-2 PEG | 1.05 MDa |
| Post-autoclave, weight average molecular weight of Hyaluranic Acid-2 PEG | 0.18 MDa |

Comparative Example B

An aqueous packaging solution was made by mixing the following components, listed in Table 14 at amounts per weight.

TABLE 14

| Ingredient | % w/w |
| --- | --- |
| Monobasic sodium phosphate monohydrate | 0.015 |
| Dibasic sodium phosphate anhydrous | 0.065 |
| Sodium Chloride | 0.999 |
| Ectoine | — |
| Hyaluranic Acid-2 PEG | 0.04 |
| Purified Water, USP | Q.S. to 100% w/w |
| Hyaluranic Acid-2 PEG starting weight average molecular weight | 2.3 MDa |
| Pre-autoclave, weight average molecular weight of Hyaluranic Acid-2 PEG | 2.07 MDa |
| Post-autoclave, weight average molecular weight of Hyaluranic Acid-2 PEG | 0.63 MDa |

Features and Advantages

1. A packaging system for the storage of an ophthalmic device comprising:
   a sealed container containing one or more unused ophthalmic devices immersed in an aqueous packaging solution comprising ectoine or an ophthalmologically acceptable ectoine derivative; wherein the aqueous packaging solution has an osmolality of at least about 150 mOsm/kg, a pH of about 6 to about 9 and is sterilized.

2. The packaging system of feature 1, wherein the ophthalmic device is a contact lens.

3. The packaging system of feature 1, wherein the ectoine is L-ectoine.

4. The packaging system of feature 1, wherein the ophthalmologically acceptable ectoine derivative is hydroxyectoine, a polyectoine, a salt thereof, an ester thereof, an oliogomer thereof or a mixture thereof.

5. The packaging system of feature 1, wherein the aqueous packaging solution further comprises one or more glycosaminoglycans.

6. The packaging system of feature 5, wherein the one or more glycosaminoglycans are selected from the group consisting of chondroitin, chondroitin sulfate, dermatan, dermatan sulfate, heparin, heparan sulfate, hyaluronan and hyaluronic acid or salt thereof.

7. The packaging system of feature 5, wherein the one or more glycosaminoglycans are hyaluronic acid or salt thereof having a weight average molecular weight ranging from about 100,000 to about 3,000,000.

8. The packaging system of feature 1, wherein the aqueous packaging solution further comprises a reaction product of a first glycosaminoglycan, a second glycosaminoglycan, and a first crosslinking agent, wherein the first glycosaminoglycan is different than the second glycosaminoglycan.

9. The packaging system of feature 8, wherein the first glycosaminoglycan and the second glycosaminoglycan are independently selected from the group consisting of chondroitin, chondroitin sulfate, dermatan, dermatan sulfate, heparin, heparan sulfate, hyaluronan and hyaluronic acid or a salt thereof.

10. The packaging system of feature 8, wherein the first glycosaminoglycan is hyaluronic acid and the second glycosaminoglycan is chondroitin sulfate.

11. The packaging system of feature 8, wherein the reaction product comprises a crosslinked structure represented by the following formula:

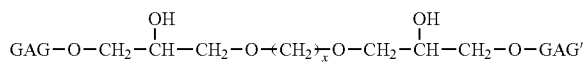

wherein GAG and GAG' are independently a glycosaminoglycan selected from the group consisting of chondroitin, chondroitin sulfate, dermatan, dermatan sulfate, heparin, heparan sulfate, and hyaluronic acid, wherein the GAG and GAG' each possess a plurality of hydroxyl groups, "GAG-O" represents a substituted hydroxyl group on the glycosaminoglycan, and x is an integer equal to 1 to 20.

12. The packaging system of feature 11, wherein GAG is hyaluronic acid and GAG' is chondroitin sulfate.

13. The packaging system of feature 8, wherein the reaction product comprises a crosslinked structure represented by the following formula

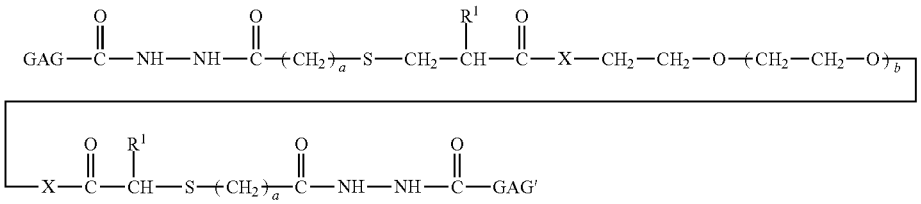

wherein GAG and GAG' are independently a glycosaminoglycan selected from the group consisting of chondroitin, chondroitin sulfate, dermatan, dermatan sulfate, heparin, heparan sulfate, and hyaluronic acid, wherein the GAG and GAG' each possess a plurality of hydroxyl groups, "GAG-C(O)" represents a substituted carboxyl group on the glycosaminoglycan, X is NH or $CH_2$ and "a" independently is an integer equal to 1 to 10.

14. The packaging system of feature 13, wherein GAG is hyaluronic acid and GAG' is chondroitin sulfate.

15. The packaging system of feature 8, wherein the reaction product comprises a crosslinked structure represented by the following formula:

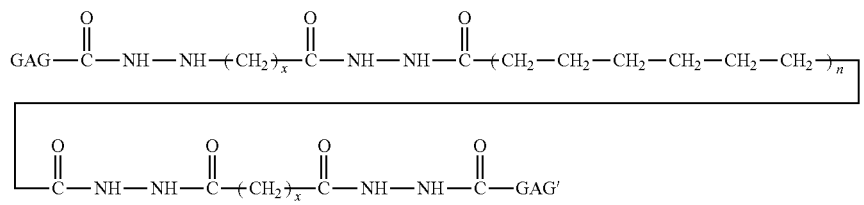

wherein GAG and GAG' are independently a glycosaminoglycan selected from the group consisting of chondroitin, chondroitin sulfate, dermatan, dermatan sulfate, heparin, heparan sulfate, and hyaluronic acid, wherein the GAG and GAG' each possess a plurality of hydroxyl groups, "GAG-C(O)" represents a substituted carboxyl group on the glycosaminoglycan, n is an integer equal to 1 to 10 and x independently is an integer equal to 1 to 10.

16. The packaging system of feature 15, wherein GAG is hyaluronic acid or salt thereof and GAG' is chondroitin sulfate.

17. The packaging system of feature 8, wherein the reaction product comprises a crosslinked structure represented by the following formula:

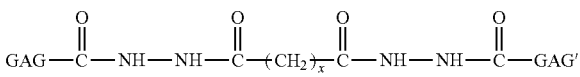

wherein GAG and GAG' are independently a glycosaminoglycan selected from the group consisting of chondroitin, chondroitin sulfate, dermatan, dermatan sulfate, heparin, heparan sulfate and hyaluronic acid or a salt thereof, wherein the GAG and GAG' each possess a plurality of hydroxyl groups, "GAG-C(O)" represents a substituted carboxyl group on the glycosaminoglycan, and x independently is an integer equal to 1 to 10.

18. The packaging system of feature 17, wherein GAG is hyaluronic acid and GAG' is chondroitin sulfate.

19. The packaging system of feature 8, wherein the first crosslinking agent is a bi- or polyfunctional crosslinking agent comprising two or more functional groups capable of reacting with functional groups of the first glycosaminoglycan and the second glycosaminoglycan.

20. The packaging system of feature 8, wherein the first crosslinking agent comprises a bis- or polyfunctional crosslinking agent selected from the group consisting of 1,4-butanediol diglycidyl ether (BDDE), 1,2-bis(2,3-epoxypropoxy)ethylene (EGDGE), ethylene glycol diglycidyl ether (EGDE), 1,2-ethanediol diglycidyl ether (EDDE), diepoxyoctane, 1,6-hexanediol diglycidyl ether, polypropylene glycol diglycidyl ether, polytetramethylene glycol diglycidyl ether, neopentyl glycol diglycidyl ether, polyglycerol polyglycidyl ester, diglycerol polyglycidyl ether, glycerol polyglycidyl ether, trimethylolpropane polyglycidyl ether, pentaerythritol polyglyglycidyl ether, sorbitol polyglycidyl ether, 1,2,7,8-diepoxyoctane, 1,3-butadiene diepoxide, pentaerythritol tetraglycidyl ether, and a polyepoxide.

21. The packaging system of feature 8, wherein the first crosslinking agent comprises a dihydrazide crosslinking agent selected from the group consisting of succinic acid dihydrazide, glutaric acid dihydrazide, adipic acid dihydrazide, pimelic acid dihydrazide, suberic acid dihydrazide, azalaic acid dihydrazide, sebacic acid dihydrazide, undecanedioic acid dihydrazide, dodecanedioic acid dihydrazide, brassylic acid dihydrazide, tetradecanedioic acid dihydrazide, pentadecanedioic acid dihydrazide, thapsic acid dihydrazide, and octadecanedioic acid dihydrazide.

22. The packaging system of feature 8, wherein the first crosslinking agent comprises a dihydric alcohol crosslinking agent selected from the group consisting of ethylene glycol, propylene glycol, butylene glycol diethylene glycol, dipropylene glycol, neopentyl glycol, 1,3-propanediol, hexylene glycol, pentylene glycol, heptylene glycol, and octylene glycol.

23. The packaging system of feature 8, wherein the first crosslinking agent comprises a polyhydric alcohol crosslinking agent selected from the group consisting of glycerin, pentaerythrite, xylitol, and galactitol.

24. The packaging system of feature 8, wherein the first crosslinking agent comprises a carbodiimide crosslinking agent of formula X—N═C═N—X, wherein each X independently is a $C_1$ to $C_6$ alkyl optionally substituted with 1-2 dialkylamino groups, or is a $C_5$ to $C_6$ cycloalkyl group.

25. The packaging system of feature 8, wherein the first crosslinking agent is selected from the group consisting of methacrylic anhydride, octeyl succinic anhydride, formaldehyde, gluteraldehyde, gluraraldehyde, acid chloride, n-hydroxysuccinimide, polyethylene glycol diacrylates, polyethylene glycol diamines, divinyl sulfone, a urea, a diisocyanate.

26. The packaging system of feature 8, wherein the reaction product comprises the first glycosaminoglycan crosslinked with the second glycosaminoglycan.

27. The packaging system of feature 26, wherein the first glycosaminoglycan crosslinked with the second glycosaminoglycan has a weight average molecular weight ranging from about 20,000 to about 6,000,000 Da.

28. The packaging system of feature 26, wherein the reaction product further comprises the first glycosaminoglycan crosslinked with the first glycosaminoglycan, and the second glycosaminoglycan crosslinked with the second glycosaminoglycan.

29. The packaging system of feature 8, wherein one or more third glycosaminoglycans are crosslinked with the reaction product with a second crosslinking agent.

30. The packaging system of feature 29, wherein the second crosslinking agent is the same as the first crosslinking agent.

31. The packaging system of feature 29, wherein the second crosslinking agent is different than the first crosslinking agent.

32. The packaging system of feature 29, wherein one or more third glycosaminoglycans are crosslinked with the crosslinked first glycosaminoglycan and second glycosaminoglycan with a second crosslinking agent.

33. The packaging system of feature 32, wherein the second crosslinking agent is different than the first crosslinking agent.

34. The packaging system of feature 32, wherein the one or more third glycosaminoglycans are independently selected from the group consisting of chondroitin, chondroitin sulfate, dermatan, dermatan sulfate, heparin, heparan sulfate, hyaluronan and hyaluronic acid or a salt thereof.

34. The packaging system of feature 34, wherein the one or more third glycosaminoglycans comprises hyaluronic acid or a salt thereof.

35. The packaging system of feature 8, further comprising a mixture comprising (a) the reaction product of the first glycosaminoglycan, the second glycosaminoglycan, and the first crosslinking agent, and (b) one or more third glycosaminoglycans.

36. The packaging system of feature 35, wherein the one or more third glycosaminoglycans are linear glycosaminoglycans.

37. The packaging system of feature 36, wherein the one or more linear glycosaminoglycans are linear hyaluronic acid or linear chondroitin sulfate.

8. The packaging system of feature 36, wherein the one or more linear glycosaminoglycans have a weight average molecular weight ranging from about 10,000 to about 3,000,000 Da.

39. The packaging system of feature 35, wherein the mixture comprises from about 1 wt. % to about 20 wt. % of the one or more third glycosaminoglycans, based on the total weight of the mixture.

40. The packaging system of feature 35, wherein the mixture comprises from about 1 wt. % to about 10 wt. % of the one or more third glycosaminoglycans, based on the total weight of the mixture.

41. The packaging system of feature 35, wherein the mixture comprises from about 1 wt. % to about 5 wt. % of the one or more third glycosaminoglycans, based on the total weight of the mixture.

42. The packaging system of feature 1, wherein the aqueous packaging solution further comprises a glycophospholipid polymer comprising a reaction product of one or more glycosaminoglycans and one or more phospholipids, and optionally one or more crosslinking agents.

43. The packaging system of feature 42, wherein the one or more glycosaminoglycans are selected from the group consisting of chondroitin, chondroitin sulfate, dermatan, dermatan sulfate, heparin, heparan sulfate, hyaluronan and hyaluronic acid or a salt thereof, and the one or more phospholipids are selected from the group consisting of phosphorylcholine, phosphorylhistidine, phosphorylproline, phosphoryl serine, α-phosphatidylcholine, α-phosphatidylethanolamine, α-phosphatidyl-L-serine, α-phosphatidylinositol, α-phosphatidic acid, α-phosphatidyl-DL-glycerol, α-lysophosphatidylcholine, sphingomyelin, and cardiolipin.

44. The packaging system of feature 42, wherein the one or more glycosaminoglycans are hyaluronic acid and the one or more phospholipids comprises phosphorylcholine.

45. The packaging system of feature 42, wherein the one or more phospholipids comprise a phosphorylcholine-containing phospholipid comprising a zwitterionic group represented by the following structure:

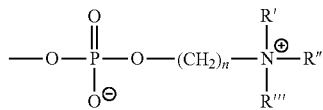

wherein n is an integer of 1 to 5 and R', R" and R'" independently of each other are a $C_1$ to $C_8$ alkyl group, a $C_1$ to $C_8$ hydroxyalkyl group or a hetero atom-containing group, and one or more reactive groups capable of reacting with the one or more one or more reactive groups capable of reacting with the one or more glycosaminoglycans and one or more crosslinking agents.

46. The packaging system of feature 42, wherein the reaction product comprises:
about 0.01 to about 50 wt. %, based on the total weight of the reaction product, of the one or more glycosaminoglycans; and
about 0.01 to about 50 wt. %, based on the total weight of the reaction product, of the one or more phospholipids.

47. The packaging system of feature 42, wherein the reaction product of the one or more glycosaminoglycans and the one or more phospholipids further comprises the one or more crosslinking agents.

48. The packaging system of feature 47, wherein the one or more crosslinking agents comprise a bi- or polyfunctional crosslinking agent comprising two or more functional groups capable of reacting with functional groups of the one or more glycosaminoglycans and the one or more phospholipids.

49. The packaging system of feature 48, wherein one or more additional glycosaminoglycans are crosslinked with the reaction product with one or more additional crosslinking agents.

50. The packaging system of feature 49, wherein the one or more additional crosslinking agents are the same as the one or more crosslinking agents.

51. The packaging system of feature 49, wherein the one or more additional crosslinking agents are different than the one or more crosslinking agents.

52. The packaging system of feature 1, wherein the aqueous packaging solution further comprises a grafted glycosaminoglycan polymer comprising a glycosaminoglycan having a polymer backbone and one or more side chains comprising a polyalkylene glycol-containing residue grafted onto the polymer backbone.

53. The packaging system of feature 52, wherein the glycosaminoglycan is selected from the group consisting of chondroitin, chondroitin sulfate, dermatan, dermatan sulfate, heparin, heparan sulfate, heparosan, hyaluronan and hyaluronic acid or a salt thereof.

54. The packaging system of feature 52, wherein the polyalkylene glycol-containing residue is derived from a polymeric compound or a salt thereof having the following structure:

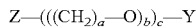

Z—(((CH$_2$)$_a$—O)$_b$)$_c$—Y wherein Z is a reactive or non-reactive end-capped group, Y is reactive functional group, a is from 2 to 6, b is from 2 to 10,000 and c is 1 or 2.

55. The packaging system of feature 54, wherein Z is selected from the group consisting of an alkoxy group, a hydroxyl group, a glycidyl group, a thiol group and an amine group, and Y is selected from the group consisting of —X—NH$_2$, —X-polydimethylsiloxane-NH$_2$, —X—SH, and —X—C(O)—R' wherein X is a linker group and R' is hydrogen or an organic moiety comprised of 1 to 20 carbon atoms.

56. The packaging system of feature 52, wherein the aqueous packaging solution further comprises a reaction product of (a) a grafted glycosaminoglycan polymer comprising a glycosaminoglycan having a polymer backbone and one or more side chains comprising a polyalkylene glycol-containing residue grafted onto the polymer backbone; and (b) one or more first crosslinking agents.

57. The packaging system of feature 56, wherein the polyalkylene glycol-containing residue of the one or more grafted glycosaminoglycan polymers is derived from a polymer or a salt thereof having the following structure:

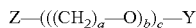

Z—(((CH$_2$)$_a$—O)$_b$)$_c$—Y wherein Z is a reactive or non-reactive end-capped group, Y is reactive functional end group, a is from 2 to 6, b is from 2 to 10,000 and c is 1 or 2.

58. The packaging system of feature 56, wherein the one or more first crosslinking agents are a bi- or polyfunctional crosslinking agent comprising two or more reactive functional groups.

59. The packaging system of feature 56, wherein the reaction product comprises:
about 0.01 to about 50 wt. %, based on the total weight of the reaction product, of the one or more grafted glycosaminoglycan polymers; and
about 0.01 to about 10 wt. %, based on the total weight of the reaction product, of the one or more first crosslinking agents.

60. The packaging system of feature 56, wherein the reaction product has a weight average molecular weight ranging from about 20,000 to about 6,000,000 Daltons (Da).

61. The packaging system of feature 56, wherein a glycosaminoglycan is crosslinked with the reaction product with a second crosslinking agent.

62. The packaging system of features 1-61, wherein the aqueous packaging solution comprises about 0.01 weight percent to about 10 weight percent, based on the total weight of the aqueous packaging solution, of the ectoine or an ophthalmologically acceptable ectoine derivative.

63. The packaging system of features 1-62, wherein the aqueous packaging solution further comprises one or more comfort agents.

64. The packaging system of features 1-63, wherein the aqueous packaging solution further comprises one or more of a poloxamer and a poloxamine.

65. The packaging system of features 1-64, wherein the aqueous packaging solution further comprises sodium chloride, potassium chloride or any combination thereof; and one or more buffer agents.

66. The packaging system of features 1-65, wherein the aqueous packaging solution further comprises one or more additives selected from the group consisting of a buffer agent, a tonicity adjusting agent, a cleaning agent, a wetting agent, a nutrient agent, a sequestering agent, a viscosity builder, a contact lens conditioning agent, an antioxidant, and mixtures thereof.

67. The packaging system of features 1-66, wherein the package is heat sterilized subsequent to sealing of the package and the aqueous packaging solution does not contain an effective disinfecting amount of a disinfecting agent or a germicide compound.

68. The packaging system of features 1-67, wherein the aqueous packaging solution does not contain an effective disinfecting amount of a disinfecting agent.

69. The packaging system of features 1-68, wherein the aqueous packaging solution does not contain a germicide compound.

70. The packaging system of feature 70, wherein the aqueous packaging solution comprises about 0.01 weight percent to about 1 weight percent, based on the total weight of the aqueous packaging solution, of one or more conjugated glycosaminoglycans.

71. A method of preparing a packaging system comprising a storable, sterile ophthalmic device, the method comprising:
(a) providing an ophthalmic device;
(b) immersing the ophthalmic device in an aqueous packaging solution according to features 1-70; wherein the aqueous packaging solution has an osmolality of at least about 150 mOsm/kg and a pH in the range of about 6 to about 9;
(c) packaging the aqueous packaging solution and the ophthalmic device in a manner preventing contamination of the ophthalmic device by microorganisms; and
(d) sterilizing the packaged solution and the ophthalmic device.

72. The method of feature 71, wherein the ophthalmic device is a contact lens.

Various features disclosed herein are, for brevity, described in the context of a single embodiment, but may also be provided separately or in any suitable sub-combination. All combinations of the embodiments are specifically embraced by the illustrative embodiments disclosed herein just as if each and every combination was individually and explicitly disclosed. In addition, all sub-combinations listed in the embodiments describing such variables are also specifically embraced by the present formulations and are disclosed herein just as if each and every such sub-combination was individually and explicitly disclosed herein.

It will be understood that various modifications may be made to the embodiments disclosed herein. Therefore, the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A packaging system, comprising:
a sealed container containing one or more unused ophthalmic devices immersed in an aqueous packaging solution comprising ectoine or an ophthalmologically acceptable ectoine derivative and a modified glycosaminoglycan; wherein the aqueous packaging solution has an osmolality of at least about 150 mOsm/kg, a pH of about 6 to about 9 and is sterilized;
wherein the modified glycosaminoglycan comprises a reaction product of a first glycosaminoglycan, a second glycosaminoglycan, and a first crosslinking agent, wherein the first glycosaminoglycan is different than the second glycosaminoglycan.

2. The packaging system of claim 1, wherein the first glycosaminoglycan is hyaluronic acid or a salt thereof and the second glycosaminoglycan is chondroitin sulfate.

3. The packaging system of claim 1, wherein one or more third glycosaminoglycans are crosslinked with the reaction product.

4. The packaging system of claim 1, wherein the ectoine is L-ectoine.

5. The packaging system of claim 1, wherein the ophthalmologically acceptable ectoine derivative is hydroxyectoine, a polyectoine, a salt thereof, an ester thereof, an oliogomer thereof or a mixture thereof.

6. The packaging system of claim 1, wherein the aqueous packaging solution comprises about 0.01 weight percent to about 10 weight percent, based on the total weight of the aqueous packaging solution, of the ectoine or the ophthalmologically acceptable ectoine derivative, and about 0.01 weight percent to about 1 weight percent, based on the total weight of the aqueous packaging solution, of the modified glycosaminoglycan.

7. A packaging system, comprising:
a sealed container containing one or more unused ophthalmic devices immersed in an aqueous packaging solution comprising ectoine or an ophthalmologically acceptable ectoine derivative and a modified glycosaminoglycan; wherein the aqueous packaging solution has an osmolality of at least about 150 mOsm/kg, a pH of about 6 to about 9 and is sterilized;
wherein the modified glycosaminoglycan comprises a glycophospholipid polymer comprising a reaction product of one or more glycosaminoglycans and one or more phospholipids.

8. The packaging system of claim 7, wherein the one or more glycosaminoglycans are hyaluronic acid or a salt thereof and the one or more phospholipids comprise a phosphorylcholine.

9. The packaging system of claim 7, wherein the ectoine is L-ectoine.

10. The packaging system of claim 7, wherein the ophthalmologically acceptable ectoine derivative is hydroxyectoine, a polyectoine, a salt thereof, an ester thereof, an oliogomer thereof or a mixture thereof.

11. The packaging system of claim 7, wherein the one or more phospholipids comprise a phosphorylcholine-containing phospholipid represented by the following structure:

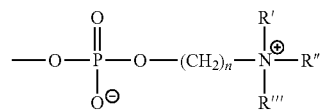

wherein n is an integer of 1 to 5 and R', R" and R''' independently of each other are a $C_1$ to $C_8$ alkyl group, a $C_1$ to $C_8$ hydroxyalkyl group or a hetero atom-containing group.

12. The packaging system of claim 7, wherein the aqueous packaging solution comprises about 0.01 weight percent to about 10 weight percent, based on the total weight of the aqueous packaging solution, of the ectoine or the ophthalmologically acceptable ectoine derivative, and about 0.01 weight percent to about 1 weight percent, based on the total weight of the aqueous packaging solution, of the modified glycosaminoglycan.

13. A packaging system, comprising:
a sealed container containing one or more unused ophthalmic devices immersed in an aqueous packaging solution comprising ectoine or an ophthalmologically acceptable ectoine derivative and a modified glycosaminoglycan; wherein the aqueous packaging solution has an osmolality of at least about 150 mOsm/kg, a pH of about 6 to about 9 and is sterilized;
wherein the modified glycosaminoglycan comprises a grafted glycosaminoglycan polymer comprising a glycosaminoglycan having a polymer backbone and one or more side chains comprising a polyalkylene glycol-containing residue grafted onto the polymer backbone.

14. The packaging system of claim 13, wherein the polyalkylene glycol-containing residue is derived from a polymer or a salt thereof having the following structure:

Z—(((CH$_2$)$_a$—O)$_b$)$_c$—Y wherein Z is a reactive or a non-reactive end-capped group, Y is a reactive functional group, a is from 2 to 6, b is from 2 to 10,000 and c is 1 or 2.

15. The packaging system of claim 13, wherein the ectoine is L-ectoine.

16. The packaging system of claim 13, wherein the ophthalmologically acceptable ectoine derivative is hydroxyectoine, a polyectoine, a salt thereof, an ester thereof, an oliogomer thereof or a mixture thereof.

17. The packaging system of claim 13, wherein the aqueous packaging solution comprises about 0.01 weight percent to about 10 weight percent, based on the total weight of the aqueous packaging solution, of the ectoine or the ophthalmologically acceptable ectoine derivative, and about 0.01 weight percent to about 1 weight percent, based on the total weight of the aqueous packaging solution, of the modified glycosaminoglycan.

18. A packaging system, comprising:
a sealed container containing one or more unused ophthalmic devices immersed in an aqueous packaging solution comprising ectoine or an ophthalmologically acceptable ectoine derivative and a modified glycosaminoglycan; wherein the aqueous packaging solution has an osmolality of at least about 150 mOsm/kg, a pH of about 6 to about 9 and is sterilized;

wherein the modified glycosaminoglycan comprises a reaction product of (a) a grafted glycosaminoglycan polymer comprising a glycosaminoglycan having a polymer backbone and one or more side chains comprising a polyalkylene glycol-containing residue grafted onto the polymer backbone; and (b) one or more first crosslinking agents.

19. The packaging system of claim 18, wherein the ectoine is L-ectoine.

20. The packaging system of claim 18, wherein the ophthalmologically acceptable ectoine derivative is hydroxyectoine, a polyectoine, a salt thereof, an ester thereof, an oliogomer thereof or a mixture thereof.

21. The packaging system of claim 18, wherein the polyalkylene glycol-containing residue of the one or more grafted glycosaminoglycan polymers is derived from a polymer or a salt thereof having the following structure:

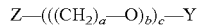

wherein Z is a reactive or non-reactive end-capped group, Y is reactive functional end group, a is from 2 to 6, b is from 2 to 10,000 and c is 1 or 2.

22. The packaging system of claim 18, wherein the aqueous packaging solution comprises about 0.01 weight percent to about 10 weight percent, based on the total weight of the aqueous packaging solution, of the ectoine or the ophthalmologically acceptable ectoine derivative, and about 0.01 weight percent to about 1 weight percent, based on the total weight of the aqueous packaging solution, of the modified glycosaminoglycan.

* * * * *